(12) United States Patent
Rapoza et al.

(10) Patent No.: US 9,572,692 B2
(45) Date of Patent: Feb. 21, 2017

(54) BIOABSORBABLE STENT THAT MODULATES PLAQUE GEOMETRIC MORPHOLOGY AND CHEMICAL COMPOSITION

(75) Inventors: Richard Rapoza, San Francisco, CA (US); Yunbing Wang, Sunnyvale, CA (US); James P. Oberhauser, Saratoga, CA (US); Syed F. A. Hossainy, Fremont, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 1347 days.

(21) Appl. No.: 12/510,076

(22) Filed: Jul. 27, 2009

(65) Prior Publication Data

US 2010/0198331 A1    Aug. 5, 2010

Related U.S. Application Data

(63) Continuation-in-part of application No. 12/364,321, filed on Feb. 2, 2009, now abandoned, and a
(Continued)

(51) Int. Cl.
*A61F 2/82* (2013.01)
*A61F 2/91* (2013.01)
(Continued)

(52) U.S. Cl.
CPC ............... *A61F 2/91* (2013.01); *A61L 31/06* (2013.01); *A61L 31/148* (2013.01); *A61L 31/16* (2013.01);
(Continued)

(58) Field of Classification Search
CPC ............... A61F 2210/0004; A61F 2250/0067
See application file for complete search history.

(56) References Cited

U.S. PATENT DOCUMENTS 6,762,418 B2   7/2004  Lambert et al.
6,899,729 B1 *  5/2005  Cox ..................... A61F 2/915
                                                  606/200

(Continued)

OTHER PUBLICATIONS

Absorb: Bioabsorbable Coronary Stents Successfully and Safely Deployed, downloaded from: www.tct2006.com/Dailies_TCT2006, Nov. 14, 2008, 1 pg.
(Continued)

*Primary Examiner* — Thomas J Sweet
*Assistant Examiner* — Cheryl Miller
(74) *Attorney, Agent, or Firm* — Squire Patton Boggs (US) LLP

(57) ABSTRACT

Methods of treating a diseased blood vessel exhibiting stenosis with a bioabsorable stent are disclosed. The implanted stent supports the section of the vessel at an increased diameter for a period of time to allow the vessel to heal. The stent loses radial strength sufficient to support the section of the vessel in less than 6 months after implantation, loses mechanical integrity, and then erodes away from the section. The biodegradable stent results in changes in properties of plaque with time as the stent degrades. The time-dependent properties include the luminal area of the plaque and plaque geometric morphology parameters.

6 Claims, 23 Drawing Sheets

Related U.S. Application Data continuation-in-part of application No. 12/506,121, filed on Jul. 20, 2009, now abandoned.

(51) Int. Cl.
  *A61L 31/16* (2006.01)
  *A61L 31/06* (2006.01)
  *A61L 31/14* (2006.01)

(52) U.S. Cl.
  CPC *A61F 2210/0004* (2013.01); *A61F 2210/0076* (2013.01); *A61F 2230/0054* (2013.01); *A61L 2300/412* (2013.01)

(56) References Cited

U.S. PATENT DOCUMENTS

| | | | |
|---|---|---|---|
| 8,182,890 B2* | 5/2012 | Zheng et al. | 428/36.9 |
| 2002/0062147 A1* | 5/2002 | Yang | A61F 2/07 623/1.13 |
| 2003/0074049 A1* | 4/2003 | Hoganson et al. | 623/1.13 |
| 2006/0135985 A1 | 6/2006 | Cox et al. | |
| 2006/0265043 A1* | 11/2006 | Mandrusov | A61B 5/02007 623/1.11 |
| 2007/0202046 A1* | 8/2007 | Dave | 424/9.41 |
| 2007/0280851 A1 | 12/2007 | Freeman et al. | |
| 2007/0283552 A1 | 12/2007 | Gale et al. | |
| 2008/0010947 A1 | 1/2008 | Huang et al. | |
| 2008/0039545 A1 | 2/2008 | Muratoglu et al. | |
| 2008/0091277 A1 | 4/2008 | Deusch et al. | |
| 2008/0299002 A1 | 12/2008 | Freeman et al. | |
| 2009/0074610 A1 | 3/2009 | Sabaria | |
| 2009/0099652 A1* | 4/2009 | Granada et al. | 623/1.46 |
| 2010/0234966 A1 | 9/2010 | Lo | |

OTHER PUBLICATIONS

Compression Test, Materials Testing Solutions, downloaded from: www.instron.us/wa/applications/test_types/compressions.aspx, Nov. 14, 2008, 1 pg.
Costa et al., "Angiographic Results of the First Human Experience with Everolimus-Eluting Stents for the Treatment of Coronary Lesions (The Future I Trial)", The Am. J. of Card. vol. 95, pp. 113-116 (2005).
Fajadet et al., "Randomized, Double-Blind, Multicenter Study of the Endeavor Zotarolimus-Eluting Phosphorylcholine-Encapsulated Stent for Treatment of Native Coronary Artey Lessions", Circulation, pp. 798-806 (2006).
Grube et al., "Six-and Twelve-Month Results from First Human Experience Using Everolimus-Eluting Stents with Bioabsorbable Polymer", Circulation, pp. 2168-2171 (2004).
Gussenhoven et al., "Intravascular Ultrasonic Imaging: Histologic and Echographic Correlation", Eur. Vasc. Surg. 3, pp. 571-576 (1989).
U.S. Appl. No. 12/506,121, filed Jul. 20, 2009, Hossainy et al.
U.S. Appl. No. 12/559,402, filed Sep. 14, 2009, Lambert et al.
Kukreja et al., "Biodegradable drug eluting stents: invasive and non-invasive imaging", Euro Intervention 2, p. 403 (2006).
Lachowitzer "Assessing Radial Tests for Endovascular Implants", Medical Device Link, downloaded from: www.devicelink.com/grabber.php3?, Nov. 10, 2008, 4 pgs.
Markman, "Absorbable coronary stents", Lancet 369, pp. 1839-1840 (2007).
Meredith et al., "First-in-human study of the Endeavor ABT-578-eluting phosphorylcholine-encapsulated stent system in de novo native coronary artery lesions: endeavor I Trial", Clinical Research, EuroInterv. 1; pp. 157-164 (2005).
Mintz et al., "Arterial Remodeling after Coronary Angioplasty: A Serial Intravascular Ultrasound Study", Circulation 94, pp. 35-43 (1996).
Ormiston et al., "A bioabsorbable everolimus-eluting coronary stent system for patients with single de-novo coronary artery lesions (ABSORB): a prospective open-label trial", Lancet 371, pp. 899-907 (2008).
Ormiston et al., "First-in-Human Impantation of a Fully Bioabsorbable Drug-Eluting Stent: The BVS Poly-L-Lactic Acid Everolimus-Eluting Coronary Stent", Catheterization and Cardiovascular Interventions 69: pp. 128-131 (2007).
Pietrzak et al., "Bioabsorbable Polymer Science for the Practicing Surgeon", The J. of Craniofacial Surgery vol. 8, No. 2, pp. 87-91 (1997).
Radial testing of Vascular Stents (ASTM F2079 and ASTM F2477), Materials Testing Solutions, downloaded from: www.instron.us/wa/solutions//Stents.aspx, Nov. 14, 2008, 1 pg.
Ramcharitar et al., "Fully Biodegradable Coronary Stents: Progress to Date", Am. J. of Card. Drugs vol. 8, No. 5, pp. 305-314 (2008) Abstract 2 pgs.
Serruys et al., "A bioabsorbable everolimus-eluting coronary stent system (Absorb): 2-year outcomes and results from multiple imaging methods", Lancet 373, pp. 897-910 (2009).
Slottow et al., "Optical coherence tomography and intravascular ultrasound imaging of bioabsorbable magnesium stent degradation in porcine coronary arteries", Cardiovasc. Revascularization Medicine 9, pp. 248-254 (2008).
Stone et al., "A Polymer-Based, Paclitaxel-Elluting Stent in Patients with Coronary Artery Disease", The New England J. of Medicine, 350; 3, pp. 221-231 (2004).
Tanimoto et al., "Comparison of in Vivo Acute Stent Recoil Between the Bioabsorbable Everolimus-Eluting Coronary Stent and the Everolimus-Eluting Cobalt Chromium Coronary Stent: Insights From the ABSORB and SPIRIT Trails", Catheterization and Cardiovascular Interventions 70, pp. 515-523 (2007).
Tanimoto et al., "Late Stent Recoil of the Bioabsorbable Everolimus-Eluting Coronary Stent and its Relationship with Plaque Morphology", J. of Am. Col. of Cardiology vol. 52, No. 20, pp. 1616-1620 (2008).
Wood "ABSORBing the Details: 12-Month Results for Bioabsorbable, Everolimus-Eluting Stent", downloaded from: www.medscape.com/viewarticle/571705, Nov. 14, 2008, 16 pgs.

* cited by examiner

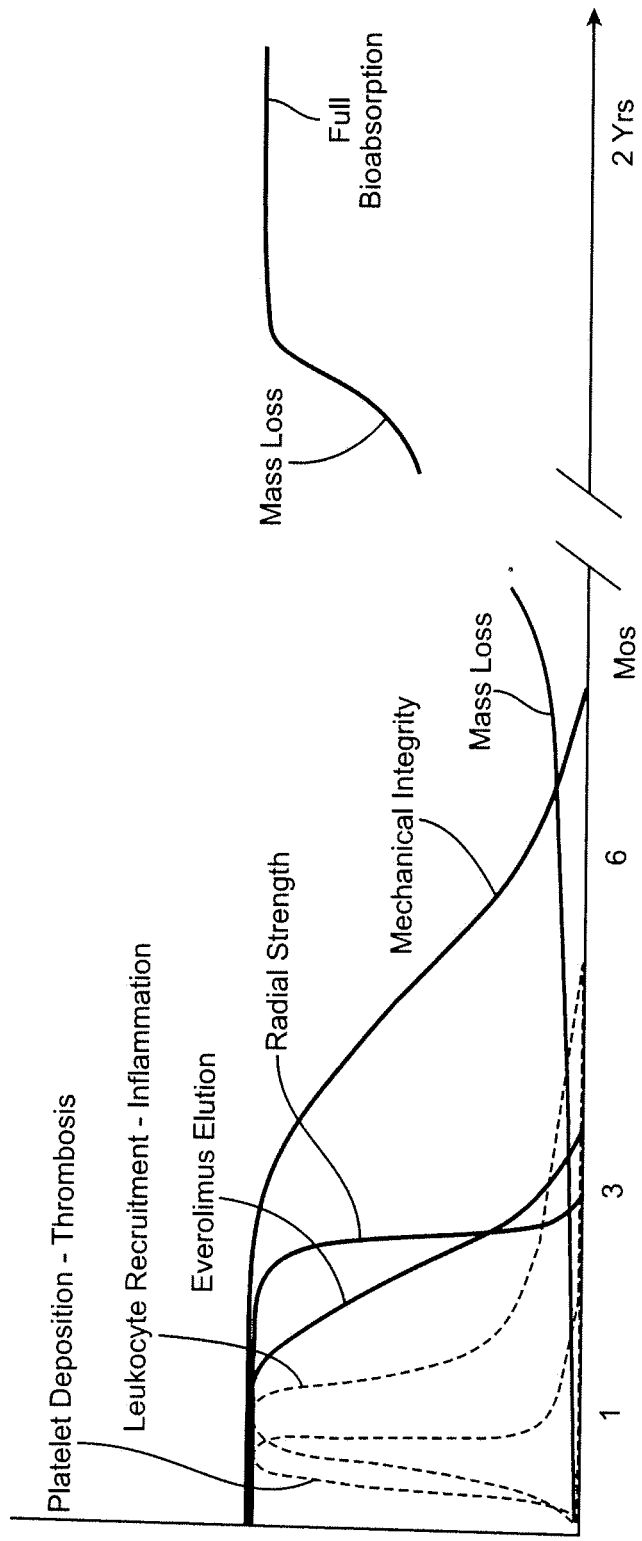

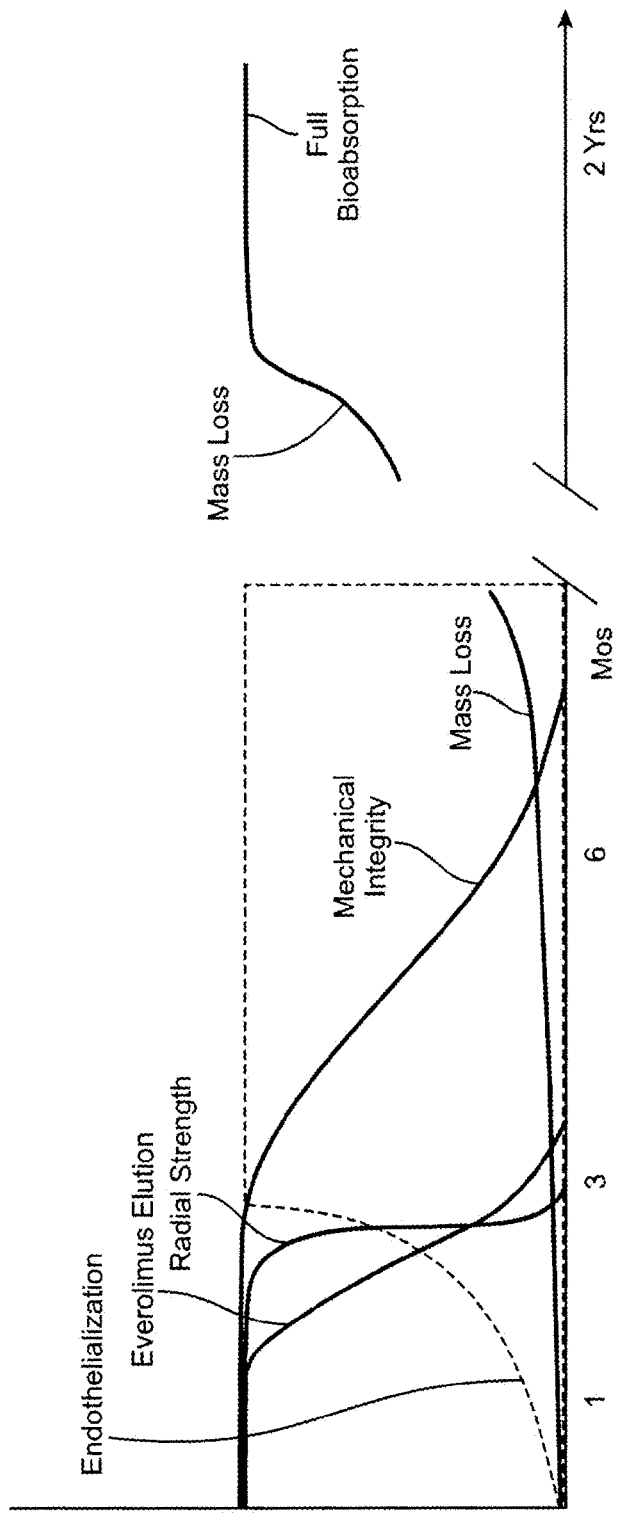

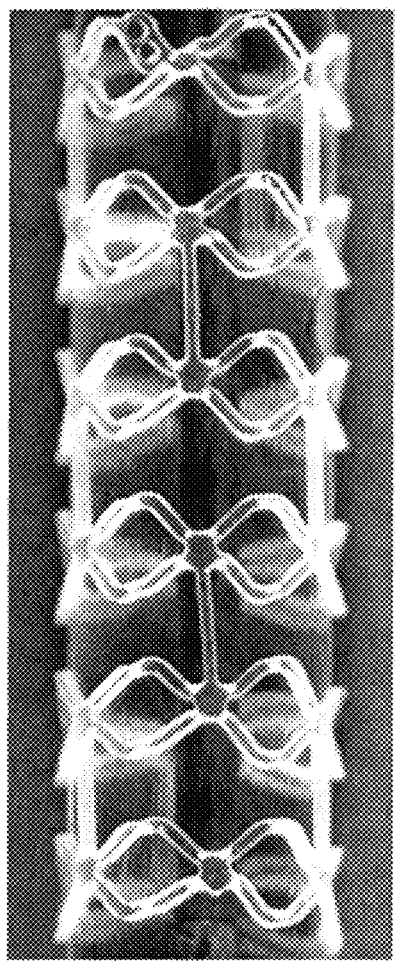
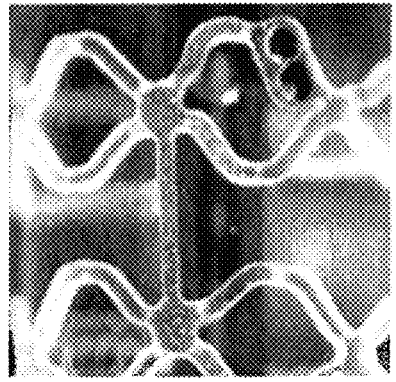
FIG. 8A
FIG. 8B

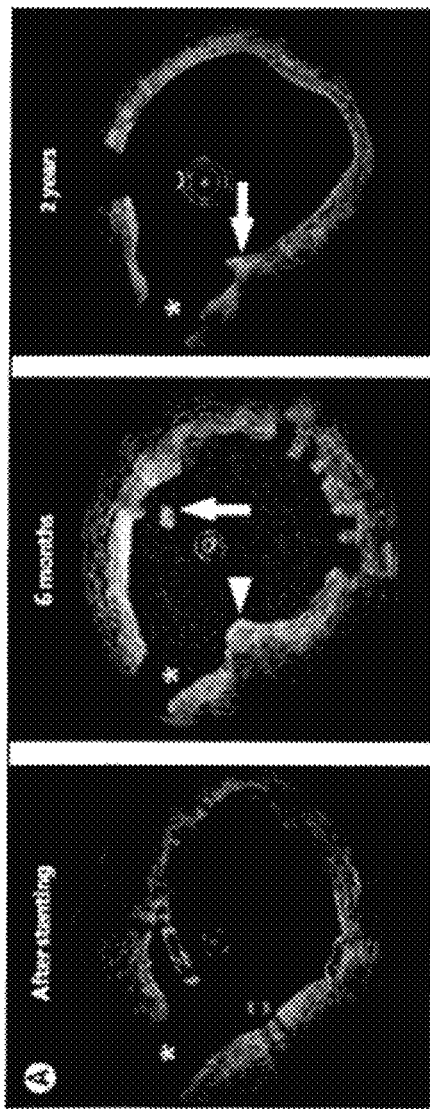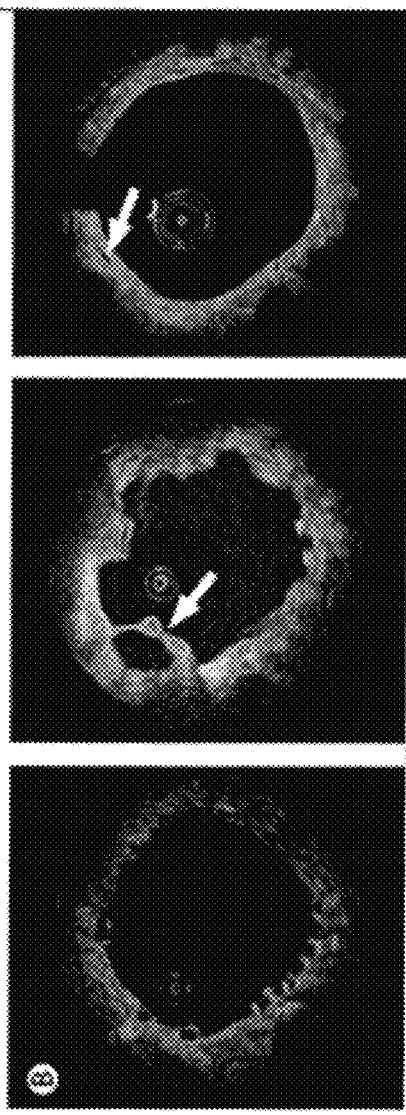
FIG. 13A
FIG. 13B

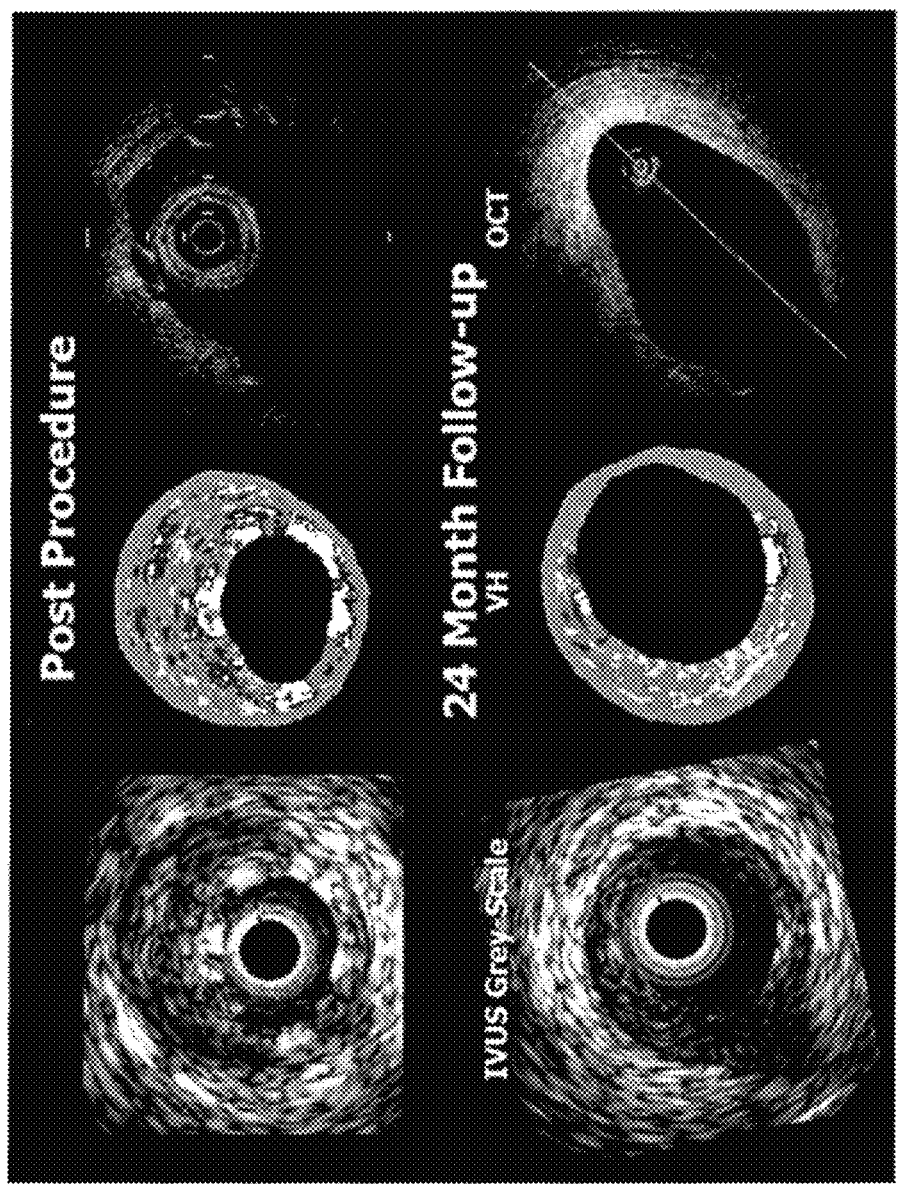

BIOABSORBABLE STENT THAT MODULATES PLAQUE GEOMETRIC MORPHOLOGY AND CHEMICAL COMPOSITION

This is a continuation-in-part of application Ser. No. 12/364,321 filed on Feb. 2, 2009 now abandoned and application Ser. No. 12/506,121 filed on Jul. 20, 2009 now abandoned, and both are incorporated by reference herein.

BACKGROUND OF THE INVENTION

Field of the Invention

This invention relates to methods of treatment of coronary artery disease with bioabsorbable polymeric medical devices, in particular, stents.

Description of the State of the Art

This invention relates to radially expandable endoprostheses, that are adapted to be implanted in a bodily lumen. An "endoprosthesis" corresponds to an artificial device that is placed inside the body. A "lumen" refers to a cavity of a tubular organ such as a blood vessel. A stent is an example of such an endoprosthesis. Stents are generally cylindrically shaped devices that function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

Stents are typically composed of scaffolding that includes a pattern or network of interconnecting structural elements or struts, formed from wires, tubes, or sheets of material rolled into a cylindrical shape. This scaffolding gets its name because it physically holds open and, if desired, expands the wall of the passageway. Typically, stents are capable of being compressed or crimped onto a catheter so that they can be delivered to and deployed at a treatment site.

Delivery includes inserting the stent through small lumens using a catheter and transporting it to the treatment site. Deployment includes expanding the stent to a larger diameter once it is at the desired location. Mechanical intervention with stents has reduced the rate of restenosis as compared to balloon angioplasty. Yet, restenosis remains a significant problem. When restenosis does occur in the stented segment, its treatment can be challenging, as clinical options are more limited than for those lesions that were treated solely with a balloon.

Stents are used not only for mechanical intervention but also as vehicles for providing biological therapy. Biological therapy uses medicated stents to locally administer a therapeutic substance. The therapeutic substance can also mitigate an adverse biological response to the presence of the stent. Effective concentrations at the treated site require systemic drug administration which often produces adverse or even toxic side effects. Local delivery is a preferred treatment method because it administers smaller total medication levels than systemic methods, but concentrates the drug at a specific site. Local delivery thus produces fewer side effects and achieves better results.

A medicated stent may be fabricated by coating the surface of either a metallic or polymeric scaffolding with a polymeric carrier that includes an active or bioactive agent or drug. Polymeric scaffolding may also serve as a carrier of an active agent or drug.

The stent must be able to satisfy a number of mechanical requirements. The stent must be capable of withstanding the structural loads, namely radial compressive forces, imposed on the stent as it supports the walls of a vessel. Therefore, a stent must possess adequate radial strength. Radial strength, which is the ability of a stent to resist radial compressive forces, is due to strength around a circumferential direction of the stent.

Once expanded, the stent must adequately provide lumen support during a time required for treatment in spite of the various forces that may come to bear on it, including the cyclic loading induced by the beating heart. For example, a radially directed force may tend to cause a stent to recoil inward. In addition, the stent must possess sufficient flexibility to allow for crimping, expansion, and cyclic loading.

The treatment of coronary artery disease with a stent may require the presence of the stent only for a limited period of time. During or part of this limited time a healing process takes place which includes changes in the structure of the vessel wall, referred to as remodeling. After the healing process is completed, the presence of the stent is no longer necessary.

Coronary stents made from biostable or non-erodible materials, such as metals, have become the standard of care for percutaneous coronary intervention (PCI) since such stents have been shown to be capable of preventing early and later recoil and restenosis. However, a stent made out of such biostable material retains is mechanical or structural integrity and remains at the implant site indefinitely unless it is removed by intervention or is dislodged. Intervention presents risks to the patient and dislodgement can have significant adverse consequences on the patient. Leaving the stent at the implant site permanently also has disadvantages. One disadvantage is that the stented segment has the compliance of the stent which is very different from that of healthy vessel segment. Another drawback of such durably implanted stents is that the permanent interaction between the stent and surrounding tissue can pose a risk of endothelial dysfunction and late thrombosis.

SUMMARY OF THE INVENTION

Various embodiments of the present invention include a method of treating a diseased section of a blood vessel, comprising: implanting a bioabsorbable polymeric stent comprising a scaffolding composed of a pattern of struts at a diseased section of a blood vessel to form a stented segment comprising the stent and a vessel wall at the diseased section, wherein the vessel wall comprises a plaque region including a necrotic core component and a fibrous component, wherein at pre-implantation and post-implantation of the stent the necrotic core component is in contact with a blood-contacting surface of the vessel wall, and wherein as the stent degrades the fibrous component becomes positioned between the necrotic core component and the blood-contacting surface of the vessel wall so that the necrotic core component is not in contact with the blood-contacting surface.

Further embodiments of the present invention include a method of treating a diseased section of a blood vessel, comprising: implanting a bioabsorbable polymeric stent comprising a scaffolding composed of a pattern of struts at a diseased section of a blood vessel to form a stented segment comprising the stent and a vessel wall at the diseased section, wherein the vessel wall comprises plaque region including a necrotic core component, and wherein as the stent degrades the area of the necrotic core component as a percentage of the total plaque region area decreases.

Additional embodiments of the present invention include a method of treating a diseased section of a blood vessel, comprising: implanting a bioabsorbable polymeric stent comprising a scaffolding composed of a pattern of struts at a diseased section of a blood vessel to form a stented segment comprising the stent and a vessel wall at the diseased section, wherein the vessel wall comprises plaque, wherein the volume and area of the plaque increases during a first time period after implantation and then decreases during a second time period after the first time period, wherein the scaffolding is completely or substantially absorbed by the end of the second time period.

Other embodiments of the present invention include a method of treating a diseased section of a blood vessel, comprising: implanting a bioabsorbable polymeric stent comprising a scaffolding composed of a pattern of struts at a diseased section of a blood vessel to form a stented segment comprising the stent and a vessel wall at the diseased section, wherein the vessel wall comprises plaque including a necrotic core component and a fibrous component, wherein between post-implantation and when the stent is completely or substantially degraded away the necrotic core component as a percentage of the plaque has decreased and the fibrous component as a percentage of the plaque has increased.

Additional embodiments of the present invention include a method of treating a diseased section of a blood vessel, comprising: implanting a bioabsorbable polymeric stent comprising a scaffolding composed of a pattern of struts at a diseased section of a blood vessel to form a stented segment comprising the stent and a vessel wall at the diseased section, wherein the vessel wall comprises a region of plaque, and wherein a radius of curvature of the surface of the plaque region during degradation of the stent is higher than a radius of curvature of the surface of the plaque region pre-implantation.

BRIEF DESCRIPTION OF THE DRAWINGS

FIGS. 5A-C represent a schematic representation of an exemplary embodiment depicting the properties of an implanted bioabsorbable stent as a function of time.
FIGS. 8A-B depict images of a bioabsorable stent used in a clinical study.

FIGS. 13A-B depicts serial assessment of stent struts by OCT.
FIGS. 16A-B, 17A-B, and 18A-B are IVUS, IVUS-VH, and OCT images, respectively, for one patient post-PCI and at 2 years follow-up.

DETAILED DESCRIPTION OF THE INVENTION

Various embodiments of the present invention relate to a bioabsorbable stent and methods of treatment of a blood vessel afflicted with coronary artery disease with the bioabsorbable stent. These embodiments include a stent and treatment with the stent which is made from a bioabsorbable polymer or polymers. In these embodiments, the stent is implanted at an afflicted site or section in the vessel, interacts with the vessel in a manner (described in detail below) that elicits time dependent healing responses from the vessel, and eventually disappears or substantially disappears from the section, which is healed. Therefore, the stent and treatment results in healing of the afflicted section without the associated disadvantages (as described in detail below) of a biostable stent.

Coronary artery disease refers to a condition in which the arteries that supply blood to heart muscle become hardened and narrowed or stenotic. This is due to the buildup of cholesterol and other material, called plaque, on their inner walls. Such narrowed or stenotic portions are often referred to as lesions. Coronary artery disease includes restenosis which refers to the reoccurrence of stenosis. Although there are probably several mechanisms that lead to restenosis of arteries, an important one is the inflammatory response, which induces tissue proliferation around an angioplasty site. The inflammatory response can be caused by the balloon expansion used to open the vessel, or if a stent is placed, by the foreign material of the stent itself.

Figure 1A:
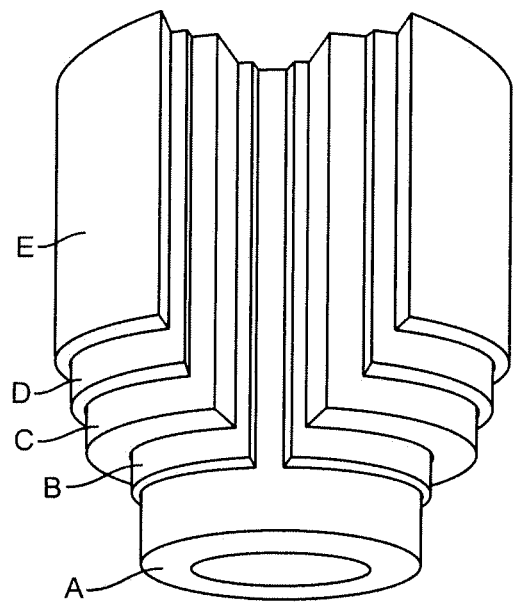
FIG. 1A depicts a radial cross-section of an artery.
Figure 1B:
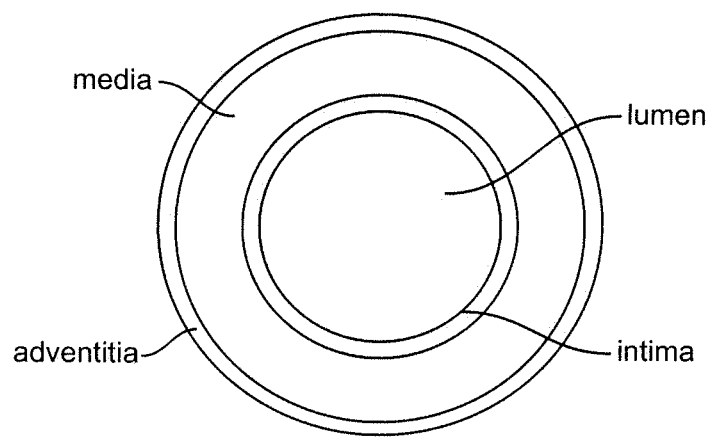
FIG. 1B depicts a section of an artery in three dimensions.

A wall of a healthy blood vessel is essentially made up of three distinct layers surrounding the lumen through which blood flows, the outermost advantitia, the media, and the intima. FIG. 1A depicts a radial cross-section of an artery and FIG. 1B depicts a section of an artery in three dimensions showing the intima (A), and the media (C), and the advantitia (E). The cells of the intima are supported by the internal elastic membrane (B) that separates the intima from the media. The external elastic membrane or lamina (D) (EEM or EEL) is a concentration of elastic fibers at the inner boundary of the adventitia and the media.

The intima layer is made up of a single layer of cells which are fat in the middle and thin at the edges. In arteries, the intima is an elastic membrane lining and includes a smooth endothelium on its inner surface that is in contact with blood flowing through the lumen. The media is the middle layer of the walls of arteries and is composed of smooth muscle and elastic fibers. The adventitia is the outermost layer of an artery. It is primarily a muscular structure contained within fibers of collagen, a strong protein which is also found in tendons and ligaments. The adventitia is therefore a very important component responsible for the inherent strength of the artery. A healthy section of a blood vessel wall includes all of these layers. However, one or both of the intima layer or endothelium in a diseased section of a blood vessel can be damaged or may not be present.

Figure 2:
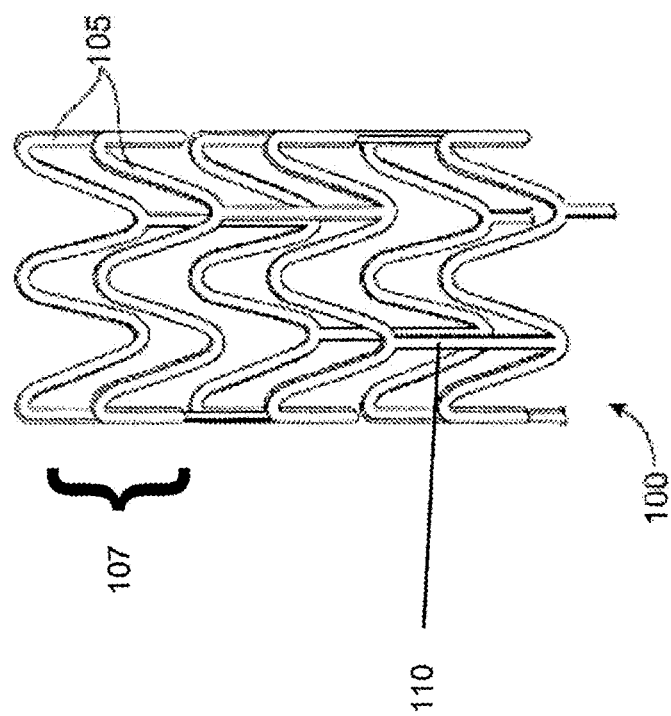
FIG. 2 depicts a stent.

A stent may include a pattern or network of interconnecting structural elements or struts. FIG. 2 depicts a view of a stent 100. In some embodiments, a stent may include a body, backbone, or scaffolding having a pattern or network of interconnecting structural elements 105. Stent 100 may be formed from a tube (not shown). FIG. 2 illustrates features that are typical to many stent patterns including cylindrical rings 107 connected by linking elements 110. The cylindrical rings are load bearing in that they provide radially directed force to support the walls of a vessel. The linking elements generally function to hold the cylindrical rings together and do not contribute significantly to the support of the lumen. The structural pattern in FIG. 2 is merely exemplary to illustrate the basic structure of a stent pattern.

A stent such as stent 100 may be fabricated from a polymeric tube or a sheet by rolling and bonding the sheet to form the tube. A tube or sheet can be formed by extrusion or injection molding. A stent pattern, such as the one pictured in FIG. 2, can be formed in a tube or sheet with a technique such as laser cutting or chemical etching. The stent can then be crimped on to a balloon or catheter for delivery into a bodily lumen.

In general, a stent can be made partially or completely from a biodegradable, bioabsorbable, or biostable polymer. A polymer for use in fabricating a stent can be biostable, bioabsorbable, biodegradable or bioerodable. Biostable refers to polymers that are not biodegradable. The terms biodegradable, bioabsorbable, and bioerodable are used interchangeably and refer to polymers that are capable of being completely degraded and/or eroded when exposed to bodily fluids such as blood and can be gradually resorbed, absorbed, and/or eliminated by the body. The processes of breaking down and absorption of the polymer can be caused by, for example, hydrolysis and metabolic processes.

In general, in order to facilitate healing of a diseased section of a vessel, the presence of a stent is necessary for only for a limited period of time. Therefore, a stent made from a biodegradable polymer is intended to remain in the body for a duration of time until its intended function of facilitating healing a diseased section of a blood vessel is completed. After the process of degradation, erosion, absorption, and/or resorption has been completed, no portion of the biodegradable stent, or a biodegradable portion of the stent will remain at the treated section of the blood vessel. In some embodiments, very negligible traces or residue may be left behind.

Reducing degradation time to the minimum time required for successful treatment is advantageous since it allows further surgery or intervention, if necessary, on a treated vessel to occur sooner. Additionally decreasing degradation time helps reduce the risk of late thrombosis.

Chemical hydrolysis of the hydrolytically unstable backbone in some polymers is the prevailing mechanism for the degradation of a bioabsorbable polymer. Other mechanisms of degradation, such as enzymatic attack and metabolic processes, can also contribute to degradation. Polymer erosion can be ideally divided into "bulk erosion" and "surface erosion." For ideal bulk erosion, polymer is chemical degraded and material is lost from the entire polymer volume.

Figure 3:
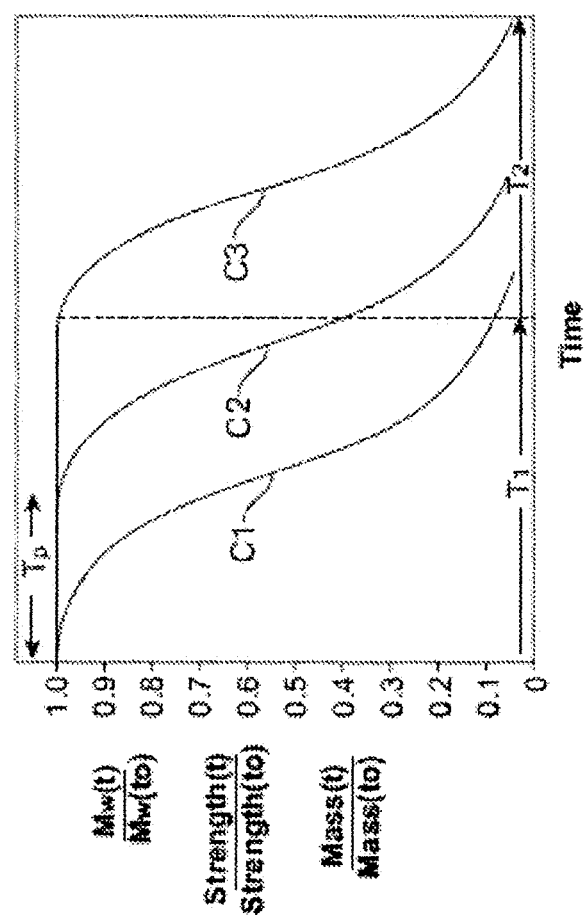
FIG. 3 depicts generic absorption curves for bulk-eroding polymers.

Although a bulk eroding polymer degrades throughout its volume, a device made from a bulk eroding polymer can still maintain its mechanical properties (e.g., strength) and mechanical or structural integrity while it degrades. FIG. 3 depicts generic absorption curves for bulk-eroding polymers showing the sequence of polymer molecular weight (C1), strength (C2), and mass reduction (C3) during degradation. Journal of Craniofacial Surgery, (8)2:89, 1997. As illustrated in FIG. 3, the degradation of a bulk eroding polymer generally occurs in two phases. In the first phase illustrated by time period T1, water penetrates the bulk of the device, preferentially attacking the chemical bonds in the amorphous phase and converting long polymer chains into shorter water-soluble fragments. The resulting decrease in molecular weight is shown by C1 in FIG. 3. For a semi-crystalline polymer, there may be a reduction in molecular weight with minimal loss in physical properties, which is illustrated by time period Tp in FIG. 3. This is because degradation occurs in amorphous phase initially and the device matrix is still held together by the crystalline regions. The reduction in molecular weight is soon followed by a reduction in mechanical properties (C2), and then erosion or mass loss (C3). The mass loss eventually results in loss of structural integrity demonstrated by fragmentation of the device. In the second phase illustrated by T2, enzymatic attack and metabolization of the fragments occur, resulting in a rapid loss of polymer mass.

Embodiments of the present invention include a bioabsorbable stent and methods of treatment of coronary artery disease with the stent. In such embodiments, a stent scaffolding can be formed from bioabsorbable material such as a bioabsorbable polymer. In particular, the stent can include a scaffolding made of bioabsorbable polymer that is designed to provide support to a vessel lumen once it is expanded. Exemplary biodegradable polymers include poly (L-lactide) (PLLA), poly(D-lactide) (PDLA), polyglycolide (PGA), and poly(L-lactide-co-glycolide) (PLGA). With respect to PLGA, the stent scaffolding may be made from PLGA between 0-100% L-lactide, in particular, 85/15 PLGA (85% L-lactide, 15% glycolide).

Additionally, the stent can further include a therapeutic coating or layer above all or a portion of the scaffolding. The coating can be composed of a bioabsorable polymer with one or more therapeutic agents dispersed or dissolved in the polymer. The therapeutic agents can include, but are not limited to, antiproliferatives, and anti-inflammatories.

Various embodiments of a method of treating diseased blood vessel include implanting or deploying the stent at a diseased site, section, or segment of a blood vessel. The diseased section can have a lesion which has caused stenosis or narrowing of the blood vessel. Implantation can be performed by positioning the stent at the diseased section and expanding the stent in apposition to the vessel walls which increases the diameter of the section of the vessel.

Figure 4A:
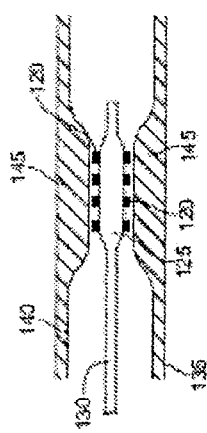
FIG. 4A depicts a cross-section of a stent and delivery system including a stent mounted on a balloon.
Figure 4B:
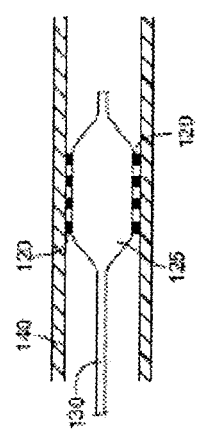
FIG. 4B shows the balloon of FIG. 4A and the stent in an expanded configuration in apposition to walls of a blood vessel.
Figure 4C:
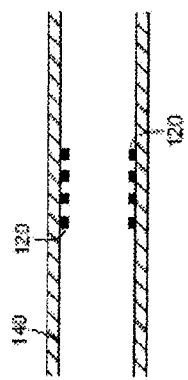
FIG. 4C shows the stent of FIGS. 4A and 4B with the balloon removed supporting a diseased section of the vessel at an expanded diameter.

In the case of a balloon-expandable stent, the stent is secured to a balloon at the end of a catheter prior to delivery and deployment. Once the secured stent is positioned at the diseased section of the blood vessel, the balloon is expanded to deploy the stent. FIG. 4A depicts a cross-section of a stent and delivery system including a stent mounted on a balloon 125 at a distal end of a catheter 130. Individual stent struts 120 are shown secured on balloon 125. The stent and delivery system are positioned within a blood vessel 135 with walls 140 at a diseased section 145. FIG. 4B shows balloon 125 and the stent in an expanded configuration in apposition to walls 140 of blood vessel 135. FIG. 4C shows the stent with the balloon removed supporting the diseased section of the vessel at an expanded diameter.

After deployment, the stent maintains patency of the diseased section for a limited period of time until chemical degradation results in degradation of the radial strength to the point that the stent can no longer support the walls of the section of the vessel. Unlike a non-erodible stent, the mechanical properties, structural integrity, and mass of the bioabsorbable stent at the stented segment are time dependent since they change during the healing process. The bioabsorbable stent provides patency to the stented segment for a finite period of time, the radial strength of the stent deteriorates, making the stent unable to continue to provide patency to the vessel walls. The loss of radial strength is followed by a gradual decline of mechanical integrity, gradual loss of mass from the stent, and eventually disappearance of the stent from the stented segment.

An essential feature of the stent of the present invention is the time dependent nature of the mechanical properties, mechanical integrity, and mass loss. The initial stent support due to the radial strength followed by its loss, the gradual loss of stent mechanical integrity, and gradual mass loss from the stent results in elicits vessel responses that allow the stented section to heal. The stent is designed so that the above stent behaviors are timed with respect to biological responses of the vessel to allow the healing processes to occur. The healed state is different from that of a permanently stented segment provided by a non-erodible stent.

During the time period that the stent provides support or maintains patency of the lumen, the stent opposes the inward radial force imposed by the lumen walls, including the cyclic loading induced by the beating heart. The stent must maintain or sustain such patency for a period of time in spite of the degradation or erosion of the stent body. An exemplary desired degree of patency is no less than 50% of the deployed diameter of the stent. Thus, the stent should have sufficient strength, stiffness (modulus), and creep resistance to keep recoil to an acceptable level during a given period. Recoil refers to a decrease in diameter of a stent from a deployed diameter. Therefore, an erodible stent structure must have the appropriate combination of mechanical properties and degradation or erosion properties to provide patency for a particular period.

In the embodiments of the present invention, the stent has design inputs that result in functional outputs that elicit healing responses of the vessel. The design inputs include, generally, mechanical, chemical, structural, microstructural properties, and the processing parameters that result in such properties. As used herein, functional outputs refer generally to two broad categories: (1) the behavior of the stent once implanted and (2) vessel outputs associate with healing. The stent outputs are associated with, elicit, or facilitate the biological responses and vessel-stent interactions.

The stent and method of treatment of the present invention has design inputs that elicit and facilitate vessel outputs that correspond to biological responses and vessel-stent interactions associated with healing. Specifically, the stent has design inputs that result in stent outputs that elicit or facilitate the healing. The vessel outputs are observable as measurements from clinical studies and demonstrate healing of the afflicted section. The changes collectively correspond to healing of the vessel.

The implantation of a bioabsorbable stent with arbitrary design inputs will inevitably elicit biological responses which change the vessel. However, an arbitrary set of design inputs will not necessarily result in vessel outputs or changes that result in one or more aspects of healing of a vessel. For example, a stent may result in formation of an endothelial layer, but not result in positive remodeling that allows for increased blood flow. Additionally, the functional outputs of an arbitrary set of design inputs can be harmful and possibly lethal to the patient. For instance, the stent may have catastrophic failure that induces a thrombo-embolitic event. The stent of the present invention elicits biological responses that result in selected aspects of a healed vessel including changes in lumen dimensions that allow increased blood flow, endothelialization, complete or partial restoration of natural vessel compliance and vasomotion. The biological responses are elicited through a synergistic combination of a set of design inputs of the stent.

Design inputs may be classified into several broad categories including, but not limited to, stent scaffolding design, material properties—stent scaffolding chemistry, material properties thermo-mechanical, material processing parameters, and therapeutic coating properties. Table 1 provides a summary exemplary design inputs for each category. The design inputs are not limited to those listed in Table 1.

TABLE 1

Design Inputs.

| Design Input Category | Design Inputs |
| --- | --- |
| Stent scaffolding design | geometry of the stent pattern |
| | strut width and thickness. |
| Materials property-scaffolding chemistry inputs | class of degradable polymer (e.g., aliphatic polyester, alpha hydroxy polyester) |
| | type of polymer (e.g., poly(L-lactide) |
| | intrinsic hydrolysis rate. |
| Material properties-thermo-mechanical inputs | molecular weight (MW) or molecular weight distribution of the scaffolding polymer |
| | mechanical properties of scaffold: radial strength, fracture toughness |
| | Tg and Tm of scaffolding polymer |
| | Degree of uniaxial (circumferential) or biaxial (circumferential and longitudinal orientation) obtained from radial expansion and/or axial elongation |
| | the degree or percent crystallinity of the scaffolding polymer |
| | size and distribution crystallites in scaffolding |
| Material processing parameters | extrusion parameters |
| | blow-molding parameters |
| | e-beam sterilization parameters |

TABLE 1-continued

Design Inputs.

| Design Input Category | Design Inputs |
| --- | --- |
| Therapeutic coating design | the type of polymer<br>type of drug<br>dose of drug in the coating<br>thickness of coating. |

Table 2 list stent outputs and exemplary design inputs which provide these outputs. The list of design inputs for each output is not limited to those listed in Table 2. The geometry of the stent pattern refers the arrangement of struts in the stent pattern (see e.g., FIG. 7). The intrinsic hydrolysis rate refers to the rate of chemical degradation of a particular type of polymer which is governed by the chemical composition of the polymer. The molecular weight distribution refers to weight average (Mw) or number average molecular weight (Mn). Degree of uniaxial (circumferential) or biaxial (circumferential and longitudinal orientation) is provided by radial expansion or radial expansion/axial elongation, respectively, of the polymer tube from which the stent is fabricated. A measure of the degree of orientation is provided by the degree or percent of radial expansion and axial elongation, respectively. The extrusion parameters are the parameters of the extrusion process for fabricating the polymer tube from which the stent is fabricated. The parameters include the temperature in the extruder, pull rate, and draw-down ratio and quenching temperature as the extrudate exits the die at the end of the extruder. The blow molding parameters include the temperature expansion and percent radial expansion and percent axial elongations.

TABLE 2

Stent outputs - properties refer to scaffolding, except for drug release profile.

| Stent Output | Design Inputs |
| --- | --- |
| Mechanical properties profile: radial strength profile, fracture toughness | class and type of polymer<br>Tg<br>uniaxial/biaxial orientation and degree of thereof<br>degree of crystallinity<br>size and distribution of crystallites<br>blow molding parameters<br>molecular weight<br>e-beam parameters<br>intrinsic hydrolysis rate |
| Drug release profile | type of coating polymer<br>type of drug<br>dose of drug in the coating<br>thickness<br>molecular weight |
| Mechanical integrity profile | class and type of scaffolding<br>uniaxial/biaxial orientation and degree of thereof<br>degree of crystallinity<br>size and distribution of crystallites<br>blow molding parameters<br>molecular weight<br>e-beam parameters<br>intrinsic hydrolysis rate |
| Erosion profile | class and type of scaffolding<br>intrinsic hydrolysis rate<br>size and distribution of crystallites |

The time dependent radial strength profile of the stent includes an initial period after intervention in which the stent maintains its radial strength to prevent negative remodeling of the vessel which is then followed by a loss of radial strength. As discussed in more detail below, the length of time the stent can provide support is particularly important in the healing, specifically, remodeling to provide increased vessel dimensions.

The radial strength loss arises from degradation of strength primarily in the bending regions of the stent scaffolding. These regions degrade and eventually are unable to oppose the force imposed by the vessel wall. The stent scaffolding then exhibits a controlled recoil inward.

The radial strength of the stent during the support period and the time dependent behavior (i.e., the loss of radial strength) are collectively due to several design inputs. These design inputs synergistically provide stent behavior that allows initial remodeling of the vessel wall with support, followed by transfer of the load to the vessel wall with further remodeling. The design inputs are listed in Table 1 for stent scaffolding design, materials property-scaffolding chemistry inputs, material properties-thermo-mechanical inputs, and material processing parameters. Design inputs include the class and type of scaffolding polymer, Tg, uniaxial/biaxial orientation and degree of thereof, degree of crystallinity, size and distribution of crystallites, blow molding parameters, molecular weight, e-beam parameters, and intrinsic hydrolysis rate. The stent of the present invention can be designed provide mechanical support between 1 and 4 months after intervention. In the clinical studies of the BVS stent discussed below, OCT images (FIG. 11) at 6 months indicate partial absorption of stent struts which indicates that support by the stent ended before 6 months.

The scaffolding polymer can be an aliphatic, semicrystalline, degradable polymer with a Tg above human body temperature, about 37° C. The semicrystalline polymer is processed to have a degree and nature of the crystallinity of a semicrystalline polymer that provides a high strength and fracture toughness. Although crystallinity provides strength to a polymer, if the crystallinity is too high, stent scaffolding can become brittle and be susceptible to fracture and failure once implanted.

Additionally, to increase the strength to weight ratio of the stent so that thinner struts can be used to reduce the stent profile, a precursor to the stent, a polymer tube, is radially expanded prior to forming a stent pattern in the tube. The polymer tube is expanded using blow molding in a temperature range that is expected yield a high nucleation density with small, well dispersed crystallites. The degree of crystallinity, nature of crystallinity, and radial orientation also increase the fracture toughness. These characteristics combined, reduces or eliminates fracture and failure of stent struts as the stent loses radial strength and reduces the chance of catastrophic failure of the stent during radial strength decline. The high fracture toughness allows for a controlled loss of radial strength during support and during loss of radial strength.

The molecular weight of the final product is designed to be high enough to provide the required radial strength and also to provide the time dependent behavior. Process parameters of process steps that degrade the molecular weight are adjusted to reduce the molecular weight degradation. These include the extrusion temperature and radiation does of the electron beam sterilization.

The drug release profile includes a release of antiproliferative drug during smooth muscle proliferation (SMP), which declines to zero to allow healing processes to occur. Specific aspects include the amount drug release and the time dependent drug release profile from the coating.

The stent of the present invention is designed to provide a release profile which controls proliferation during smooth muscle cell proliferation, but terminates soon enough to allow complete or almost complete endothelialization prior to substantial mass loss and mechanical integrity loss. "Almost complete" can correspond to at least 90% of struts covered by an endothelial layer. Specifically, the stent is designed to have a drug release profile that declines to zero between 3-4 months after intervention. As indicated below, stent is designed to allow for complete or almost complete endothelialization of stent struts between 4 and 6 months after intervention.

The design inputs include, but are not limited to, the type of polymer, type of drug, dose of drug in the coating, thickness, and molecular weight. The type of polymer is faster eroding than the scaffolding polymer, and a high fracture toughness. An exemplary polymer is an amorphous polymer (contributes to faster erosion and higher fracture toughness) with a faster intrinsic hydrolysis (for faster erosion), such as poly(DL-lactic acid). The drug-polymer ratio is relatively high to reduce the required thickness of the coating, for example, between 40-60 wt % drug. The thickness of the coating is less than 3 microns and preferably less than 2 microns. The low thickness also reduces the profile of the stent which limits the likelihood of thrombosis. A molecular weight lower than the scaffolding polymer contributes to faster erosion rate. A weight average molecular weight of the coating is between 40,000 and 80,000.

Mechanical integrity refers to the size, shape, and connectivity of the structural elements of the stent. For example, the shape refers to the generally tubular shape of the stent formed by the cylindrically-shape rings connected by the linking elements of the pattern.

An initial loss of mechanical integrity occurs when some or all of the linking elements have failed resulting in partial or complete loss of connectivity between cylindrical rings. The cylindrical rings can remain intact for a period of time and maintain a circular shape. Further loss of mechanical integrity occurs when there is a loss of connectivity between structural elements in the cylindrical rings.

The stent of the present invention is designed to exhibit features of mechanical integrity profile that are critical to vessel outputs associated with healing. The mechanical integrity is maintained a sufficient time to enable endothelialization (e.g., between 90-100% of struts covered) within 4-6 months after intervention. Additionally, the stent is designed to provide a gradual loss mechanical integrity after loss of radial strength to provide a restoration of vessel compliance and vasomotion.

The mechanical integrity profile of the stent is due to several design inputs which synergistically provide the profiles that provide the vessel outputs associated with healing. These mechanical integrity arises from several design inputs listed in Table 1. These stent inputs relate to stent scaffolding design, materials property-scaffolding chemistry inputs, material properties-thermo-mechanical inputs, and material processing parameters.

Stent inputs include class and type of scaffolding polymer, uniaxial/biaxial orientation and degree thereof, degree of crystallinity, size and distribution of crystallites, blow molding parameters, molecular weight, e-beam parameters, and intrinsic hydrolysis rate. The chemistry and molecular weight of the scaffolding polymer contribute to the timing of the mechanical integrity and erosion profile.

As illustrated in FIG. 2, mass loss can be insignificant even after strength is lost and after a significant loss of molecular weight. The mechanical integrity and erosion profiles depend at least on the intrinsic hydrolysis rate of the polymer (class and type) and on the initial molecular weight of the scaffolding. The mechanical integrity profile also depends the strength and fracture toughness and factors related to these such as uniaxial/biaxial orientation and degree of thereof, degree of crystallinity, size and distribution of crystallites, and blow molding parameters. The strength and fracture toughness and the contributing factors influence the manner and timing of the breaking put of the stent pattern. The high strength and fracture toughness enables the scaffolding to hold its shape and break apart in a controlled manner with a low risk of thrombosis. For example, as discussed in more detail below, the stent scaffolding should maintain mechanical integrity until there is complete or almost complete endothelialization.

Furthermore, it is expected that the size and distribution of crystallites contribute to gradual loss of mechanical integrity. The crystallites act as tie points or crosslinks that can help hold together the polymer even after molecular weight loss.

Additionally, the integrity of the rings of the stent pattern should be maintained until at least partially incorporated into the vessel wall. The stent struts of the rings remain connected until incorporated into a vessel wall by the endothelial layer. Additionally, the formation of the endothelial layer and the manner and timing of stent pattern break-up depends on the cross-sectional size of the struts (i.e., the thickness and width of the struts) and the fracture toughness and strength of specific portions of the pattern. A larger strut cross-section provides higher strength and delays pattern break-up, however, the struts with a larger cross-section present a large profile to blood flow and take longer for the endothelial layer to incorporate. With regard to the latter, the links can be designed to fail first, leaving the rings to fail after endothelialization and absorption into vessel wall.

In the clinical studies of the BVS stent discussed below, reduction in molecular weight and mass had occurred to such an extent 2 years after intervention that struts were no longer recognizable by intravascular ultrasound, leaving behind few visible features. A third of stents were no longer discernible by OCT.

The stent is designed to have an erosion profile such that there is insignificant mass loss until after loss of the radial strength, mechanical integrity, and endothelialization. The stent is further designed so that there is complete absorption or incorporation of remaining struts into the vessel walls by 2 years after intervention. The erosion profile is provided by a synergistic combination of several design inputs. The class and type of polymer determine the rate at which the molecular weight, strength, and mass is lost by an arbitrary volume of polymer in the scaffolding. The erosion profile also depends on the crystallinity and size and distribution of crystallites. This is because hydrolysis is faster in amorphous regions than crystalline regions. In the clinical studies of the BVS stent discussed below, the OCT data in FIG. 15C suggest that the struts are almost or completely dissolved at 2 years.

Figure 5B:
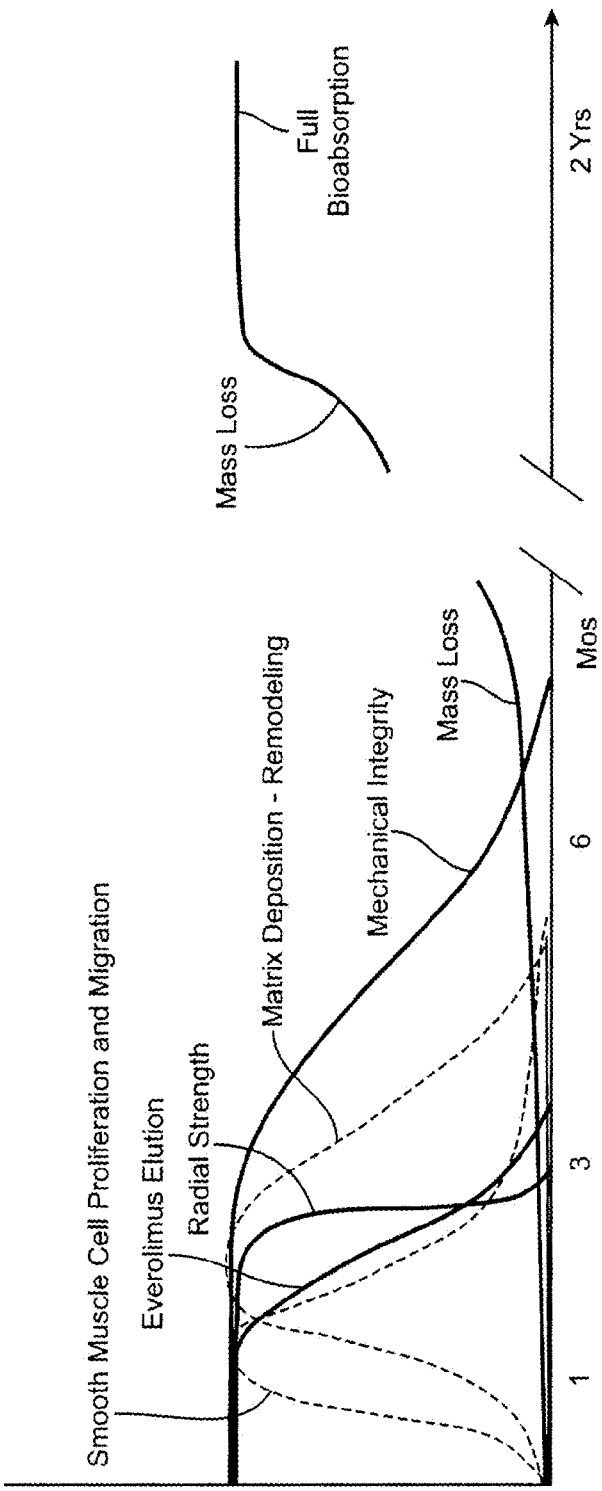

FIGS. 5A-C depict a schematic representation of exemplary time dependent behavior of a bioabsorbable stent after intervention at an afflicted section of a vessel. In addition, FIGS. 5A-C also show expected biological responses of the vessel to the stent as a function of time. Although the time scale shown is exemplary, the time dependence of stent behavior is a qualitative representation of the behavior the bioabsorbable stent of the present invention which elicits healing of the afflicted section.

Each of FIGS. 5A-C shows the time dependence of the stent properties, the radial strength, drug release, mechanical integrity, and erosion or mass loss. The radial strength of the stent is maintained for a period of time (in this case, between 2.5-3 months after intervention) after intervention during which the stent supports the vessel walls. The stent then experiences a rapid deterioration in radial strength, due to molecular weight loss, and can no longer support the lumen walls (in this case, about 3 months after intervention). The drug release is maintained at a relatively constant level after intervention (in this case, between 1-1.5 months after intervention) followed by a relatively rapid decline to zero (in this case, between 3-4 months after intervention). The mechanical integrity is maintained at a relatively constant level for a period of time after intervention (in this case, about 3-4 months after intervention) followed by a gradual decline until a complete loss at a time greater than 6 months. The period of mechanical integrity retention is longer than radial strength retention and the rate of decline of mechanical integrity is more gradual.

FIGS. 5A-C shows that that is insignificant mass loss until loss of the radial strength and mechanical integrity. Complete mass loss or full bioabsorption occurs after about two years after intervention.

There are several phases of biological response and vessel changes due to the intervention of the stent. The time period from intervention to about 1-3 months after intervention is referred to as the acute phase. FIG. 5A depicts two biological responses to the stent that occur during this phase, platelet deposition and leukocyte or white cell recruitment. These biological responses can dissipate quickly if there is growth of cellular layers over the stent. In FIG. 5A, platelet deposition peaks after two weeks and decays to a negligible level at about two months. Leukocyte recruitment peaks at slightly after one month, decreases rapidly, and trails off to zero at about five months.

FIG. 5B depicts additional biological responses during the acute phase, smooth muscle cell proliferation (SMP) and matrix deposition. SMP occurs at the inner surface of the vessel wall in the stented section. The exemplary profile in FIG. 5B shows that the smooth muscle cell proliferation reaches a peak between one and two months and then decreases to negligible levels at about five months. Smooth muscle cell proliferation can be explained with reference to the structure of an arterial wall. During smooth muscle cell proliferation, smooth muscle cells migrate from the media layer to the vessel wall surface and proliferate to form a neointima layer. Smooth muscle cell proliferation is expected to occur during a time period up to about three months after implantation of the stent. As explained below, smooth muscle cell proliferation must be controlled since it can lead to excessive and undesirable narrowing of the stented segment.

Matrix deposition involves deposition of collagen and elastin in the neointima layer, reinforcing the layer which enables it to provide mechanical support. Matrix deposition is a key component of the remodeling process. Remodeling refers to a biological response that results in modification of the neointima layer formed from smooth muscle cell proliferation. The modification facilitates a restoration of normal function of the vessel. The remodeled neointima layer includes a smooth muscle cell matrix banded together with elastin and collagen. The remodeling process is expected to start within about a week after intervention and can occur up to about 6 months or beyond 6 months after implantation.

Another biological response to the stent includes formation of an endothelial layer over the neointima layer and the stent. FIG. 5C, which depicts cumulative endothelialization as a function of time, shows that endothelialization starts shortly after implantation and reaches a maximum just before three months. A stent that allows for complete or almost complete endothelial coverage in an appropriate time frame is essential since the endothelial layer facilitates healing of the diseased section.

The stent of the present invention has design inputs and stent outputs that elicit vessel outputs that are associated with healing. The specific features of these vessel outputs are discussed below. Table 3 lists vessel outputs and the stent outputs and design inputs that correspond to the vessel outputs.

TABLE 3

Vessel Outputs.

| Vessel Output | Stent outputs |
|---|---|
| Remodeling with support to prevent elastic recoil | Radial strength profile |
| Controlled Smooth Muscle Cell proliferation | Drug release profile |
| Endothelialization | Drug release profile |
| | Mechanical integrity |
| | Erosion profile |
| Restoration of vessel compliance and homogeneity | Radial strength profile |
| | Mechanical integrity profile |
| Time dependent changes in vessel dimensions - diameter, area, volume, etc. | Drug release profile |
| | Mechanical integrity |
| | Erosion profile |
| Restoration of vasomotion | Radial strength profile |
| | Mechanical integrity profile |
| | Erosion profile |

As indicated above, an essential feature of the stent is the time dependent nature of the mechanical properties, specifically, the stent provides support through its radial strength for an initial period after intervention. This initial period of support is necessary to allow sufficient time for the neointimal layer to remodel at an increased diameter. Without sufficient remodeling time with support, the vessel will be unable to heal properly, i.e., to be restored to a natural functioning state. However, it is also essential for the radial strength decline in a controlled manner at some point so that the vessel can complete the healing process and revert to the natural functioning state.

The stent of the present invention is designed to provide support or patency to the stented section of a vessel for a limited period of time. The support of the stent prevents elastic recoil and negative remodeling, referring to remodeling at a decreased diameter. The stent provides a scaffold to maintain a circular lumen while the vessel remodels and molds itself to the stented diameter. Negative remodeling can result in vessel dimensions, such as diameter and lumen area, after stent absorption that is substantially less than a normal, healthy vessel.

The support is primarily due to the radial strength of the stent so the stent is designed to have a radial strength that is sufficient to provide this support. The stent is additionally designed to lose radial strength after the period of support so that it is no longer able to support the lumen. The loss of radial strength represents a transition of the load bearing from the stent to the partially remodeled neointimal layer, allowing completion of the healing process. Additionally, the stent is designed to maintain radial strength and lose radial strength without catastrophic failure which could result in an adverse thrombotic event.

After a period of time of mechanical support, the radial strength of the stent rapidly deteriorates to a degree that the stent can no longer provide support to the vessel walls. In some embodiments, the time period of support can be less than 1, less 3 months, or less than 6 months after intervention. However, the remodeling that occurs during the period of mechanical support is sufficient to allow the vessel to heal. In particular, the vessel walls can maintain an increased diameter after the stent disappears from the vessel.

Although smooth muscle cell proliferation is an essential feature of the remodeling process, it is necessary to control the proliferation of smooth muscle cells. In the absence of control, the smooth muscle cell layer can be undesirably thick, causing restenosis. Therefore, the stent is designed to release of an antiproliferative agent from a therapeutic coating layer over the stent scaffolding to control the smooth muscle cell proliferation. The therapeutic agent release can occur up to two or four months from intervention.

The time period of release is critical. It is important to control the proliferation of the smooth muscle cells with the antiproliferative agent. On the other hand, it is also important, as explained below, to achieve partial or complete endothelialization of the stent surface early in the healing process. In particular, it is essential to achieve partial or complete endothelialization prior to substantial loss of mechanical integrity and mass loss since the antiproliferative agent tends to inhibit endothelialization.

The endothelialization plays a critical role in the healing process with a bioabsorbable stent. Both the degree of endothelialization and timing of the endothelialization with respect the stent behavior are crucial outputs. Endothelialization refers to coverage of a surface with a layer of endothelial cells. Complete or almost complete endothelialization of the vessel wall and stent struts is essential to prevent thrombosis associated with blood contacting stent surfaces, incomplete strut apposition (persistent or late-acquired), and dislodgement of stent material. Additionally, the timing of the endothelialization with respect to mechanical integrity loss and mass loss is also an important aspect of the healing process.

The presence of a blood-contacting surface of a foreign body regardless of level of hemo-compatibility, such as a stent, presents the risk of thrombosis. In general, an endothelial layer plays a crucial role in reducing or preventing vascular thrombosis and intimal thickening. Specifically, the endothelial layer reduces or prevents deposition of proteins on the vessel wall or stent struts. Such deposition can contribute to or increase risk of thrombosis. Therefore, early and complete endothelialization of the vessel wall and stent are essential.

Incomplete stent apposition can creates a risk of thrombosis. Incomplete apposition can occur at intervention and persist for several months. Additionally, stent struts can dislodge from complete apposition with the vessel wall after intervention and is referred to as late-acquired stent apposition (LAISA). In either case, stent struts protrude into the lumen, presenting a obstacle to blood flow and risk of a thrombo-embolitic event. Incomplete apposition can occur in nonerodible stents and before loss of radial strength and mechanical integrity in a bioabsorbable stent. However, LAISA can become pervasive with a bioabsorbable stent when radial strength and mechanical integrity decline. With the decline of radial strength, the vessel can push back on the stent struts, resulting in creep of the struts inward. The development of an endothelial layer over the stent and vessel wall reduces or prevents such adverse events since the biocompatible endothelial layer covers dislodged struts.

In the BVS clinical studies, OCT images in FIGS. 13A-B show that persistent incomplete and late acquired incomplete apposition detected at 6 months and previously reported, were no longer detectable at 2-year follow-up. At 2 years, there was a smooth appearance of the endoluminal lining without strut malapposition since struts have been absorbed. Since no thrombo-embolitic events were detected, it is believed that the endothelial lining inhibited such events.

Additionally, as mechanical integrity declines and mass is lost from the stent, there is increased risk of stent material dislodging and completely separating from the vessel wall into the blood stream, which can cause a thromo-embolitic event. Endothelial layer coverage reduces or prevents such complete separation as mechanical integrity and mass is lost. Therefore, it is crucial for the complete or almost endothelialization prior to substantial loss of mechanical integrity and mass loss. Such substantial loss of mechanical integrity can include pieces of the stent struts.

As indicated above, the timing of the complete or almost complete endothelialization relative to radial strength loss, mechanical integrity loss, and mass loss is crucial. Complete or almost complete endothelialization should occur between 4 and 6 months to reduce the risk of or avoid the thrombo-embolitic events associated with LAISA and dislodgement of material in the vessel. Endothelialization prior to substantial mass is important since release of acidic hydrolytic degradation products inhibit endothelialization.

The stent of the present invention is designed to have drug release, mechanical integrity, and erosion profiles that enable endothelialization which reduces or prevents thrombo-embolitic events, in particular, those associated with LAISA and material dislodgement. The antiproliferative drug release rapidly declines to zero by 3 to 4 months after implantation so as not to interfere with endothelial growth. Additionally, the mechanical integrity remains substantially intact until about _2_ to _6_ months until the complete or almost complete endothelialization. The erosion profile is such that significant mass loss starts only after endothelialization is complete or almost complete.

The growth of the endothelial layer is facilitated by the biocompatibility of stent material. Materials that have no or a low degree of cytotoxicity are biocompatible and can result in rapid endothelial growth and healing. Biocompatible polymers include, but are not limited to, poly(L-lactide), poly(DL-lactide), polyglycolide, poly(L-lactide-co-glycolide) and polycaprolactone. In a human patient, endothelial layer growth can occur between post-stenting to 3 months, or up to six months, or more than six months after implantation. In some embodiments, at least 90%, 95%, or at least 99% of stent struts can be covered by an endothelial layer by six months after implantation.

As indicated in Table 3, the stent of the present invention allows for restoration of vessel compliance and homogeneity to that the vessel. The compliance of a segment of a vessel is the change in luminal area per unit change in distending pressure in the vessel. A segment refers to a longitudinal section of a vessel with or without the presence of a stent. Thus, as used herein, compliance of a stented segment is the compliance of the composite structure that includes both the stent and the vessel. In the absence of a stent, the segment has the compliance of the vessel walls.

OCT imaging data from the clinical studies of the BVS stent show absorption of the stent into artery walls and that the blood vessel lining of arteries treated with the stent looks more uniform after two years than it did immediately post-treatment.

The compliance of a stented segment in a treatment with the stent of the present invention changes with time. The change in the compliance is due both to the time dependence of stent properties and to the changes in the vessel wall with time. As discussed above, the radial strength, mechanical integrity, and mass of stent change as a function of time. The changes in the vessel with time are primarily due to the remodeling of the vessel wall.

The compliance at intervention is very low due to the strength and stiffness of the stent. The compliance eventually converges to that of the natural compliance of the vessel when it is healed. The compliance of the stented segment is dominated by the stent during the period of support by the stent. This is followed by a rapid increase in compliance when the radial strength of the stent declines. As the mechanical integrity of the stent declines and the stent gradually erodes, the compliance of the stented segment gradually is restored to that of a healed vessel.

As indicated above, the vessel wall is undergoing remodeling during the period of support during which the stent dominates the compliance. However, the vessel walls are also undergoing remodeling as the compliance of the stented segment changes and converging to that of the healed vessel. Even after the decline of radial strength and before the loss of structural integrity, the scaffolding can still restrict or inhibits freedom of movement of the vessel wall in response to change of pressure in the vessel. The degree of restricting gradually decreases as the scaffolding breaks up and erodes. Since the compliance is converging to the vessel wall, the vessel wall is undergoing movement or vasomotion as it is remodeling.

The clinical palpography data for the BVS stent presented below in Table 10 demonstrate that compliance convergence. The deformability of the stented segment increased significantly from intervention to 6 months follow-up and then increased slightly from 6 months to 2 years follow-up.

The stent of the present invention further provides for partial or complete restoration of vasomotion in a healed state. Vasomotion refers to rhythmic oscillations in vascular tone caused by local changes in smooth muscle. The stent outputs and design inputs that provide convergence of the compliance of the stented segment further allow for restoration of vasomotion.

Based on clinical results presented below for the BVS stent in FIGS. 20A-B, previously stented portion of arteries demonstrated the ability to expand and contract in a manner similar to a vessel that has never been stented. Additionally, the OCT data of the BVS clinical data showed an optically homogeneous vessel wall structure that, taken together with the documented restoration of vasomotion, suggests healing of the artery.

The gradual convergence of the compliance is facilitated by the mechanism of mechanical integrity loss. As discussed above, the circular rings of the pattern can be decouple and remain intact as the links fail. The stented segment returns to a natural state as the circular rings gradually break apart, incorporated into the vessel wall, and are slowly absorbed. IVUS with echogenicity, IVUS with virtual histology, and OCT results for the clinical study of the BVS stent indicate that by 2 years, the BVS stent was incorporated into the vessel wall and bioabsorbed.

The convergence of the compliance of the stented segment to that of a vessel is collectively due to several design inputs. The stent inputs, listed in Table 1, include stent scaffolding design, materials property-scaffolding chemistry inputs, material properties-thermo-mechanical inputs, and material processing parameters.

Design inputs such as the chemistry and initial molecular weight of the scaffolding provide the degradation profile of the molecular weight, radial strength, and mass. The stent is designed to have high radial strength and fracture toughness so that the stent can lose radial strength without catastrophic failure and so that the rings can remain intact, be absorbed in the vessel wall, and gradually disintegrate. The design inputs that contribute to high radial strength and fracture toughness are discussed above. Additionally, the stent scaffolding is designed to have hoop or circumferential strength that is greater than the strength transverse to the circumferential direction. This is due to greater preferential polymer chain orientation in the circumferential direction than the transverse direction. The greater preferential orientation produced through. This difference in strength facilitates failure of links that decouple adjacent rings. This decoupling allows movement of the vessel wall similar to an unstented vessel as the vessel heals.

As indicated in Table 3, the time dependent stent changes in vessel dimensions of a vessel are related to stent outputs including drug release profile, radial strength profile, mechanical integrity profile, and erosion profile. The drug release profile controls smooth muscle cell proliferation and prevents restenosis. The drug release decays early enough to allow endothelialization. The radial strength profile provides support for a period of time to prevent negative remodeling of the vessel wall followed by a rapid loss of radial strength. The mechanical integrity declines gradually, during which further remodeling takes place. Thus, each of these stent outputs influences the vessel dimension as a function of time.

Based on the clinical results presented below for the BVS stent, the radial strength was lost between intervention and 6 months. There was a significant loss of mechanical integrity by 6 months follow-up. The IVUS data in Table 8 show that the minimal luminal area, average luminal area, and lumen volume decrease from intervention and 6 months. The IVUS data showed these parameters increased between 6 months and 2 years after intervention.

OCT data in Table 11 indicates a decrease in mean lumen area, minimal lumen area, lumen volume, and mean lumen diameter from intervention to 6 months follow-up. Like the IVUS results, between 6 months and 2 years, OCT showed an increase in these quantities.

The design inputs that provide the above-described stent and vessel outputs are as described below. The Tg of the scaffolding polymer is preferably between 10 and 30° C. above Tg to insure stiffness at human body temperature. For example, PLLA has a Tg of about 60° C. The degree of crystallinity that contributes to radial strength is 25-50%. The range of radial expansion is 300 to 500%, as defined below. The temperature range of radial expansion depends on the particular polymer. However, the temperature range is in a range that is less than Tg+0.6×(Tm−Tg). Additionally, the polymer tube from which the stent is made is extruded so that it has a crystallinity of less than 15% so most of the crystallinity of the stent scaffolding can be generated in the manner described above. The weight average molecular weight range of the scaffolding struts is between 50,000 and 300,000. The range of width and thickness of the struts is 100 to 200 microns. The range of cross-sectional area is about 17,000 to 40,000 square microns.

As indicated above, hardening and narrowing of arteries is attributed to the buildup of cholesterol and plaque on the inner walls of a vessel. The morphology and composition of plaque can be characterized as having four tissue components: necrotic core, dense calcium, fibro-fatty, and fibrous tissue. The volume and cross-sectional area of these various components can be measured by analytical techniques that are described below. The plaque region can extend completely or partially around the circumference of the vessel wall.

The necrotic core of the plaque is formed inside of the vessel wall when it starts to undergo apoptosis or necrosis. The necrotic core has essentially no living cells and mainly includes cholesterol debris, such as cholesterol crystals and dead cell debris. The necrotic core is known to be vulnerable to rupture which can result in blood clot formation.

Fibro-fatty plaque is characterized by an accumulation of lipid-laden cells underneath the intima of the arteries, typically without narrowing the lumen due to compensatory expansion of the bounding muscular layer of the artery wall. Beneath the endothelium there is a "fibrous cap" covering the atheromatous "core" of the plaque.

Fibrous plaque is localized in the intima, within the wall of the artery resulting in thickening and expansion of the wall and, sometimes, spotty localized narrowing of the lumen. The fibrous plaque contains collagen fibers (eosinophilic), precipitates of calcium (hematoxylinophilic), and, rarely, lipid-laden cells. The fibrous component forms a fibrous cap that separates the other plaque components from the blood pool. The fibrous cap can become thinner resulting in exposure of unstable necrotic core close to or at the surface of the plaque.

The biodegradable stent of the present invention results in changes in properties of plaque with time as the stent degrades. This has been demonstrated by clinical results presented herein. Stent outputs and design inputs provide for the time dependent behavior of these properties.

The time dependent behavior includes the change in the luminal area and volume of the plaque as the stent degrades between implantation and 2 years, at which time the stent is almost completely eroded away. The plaque volume and area have been shown to increase over the first 6 months after implantation and then decrease between 6 months and 2 years, when the scaffolding is completely or substantially absorbed.

Figure 10:
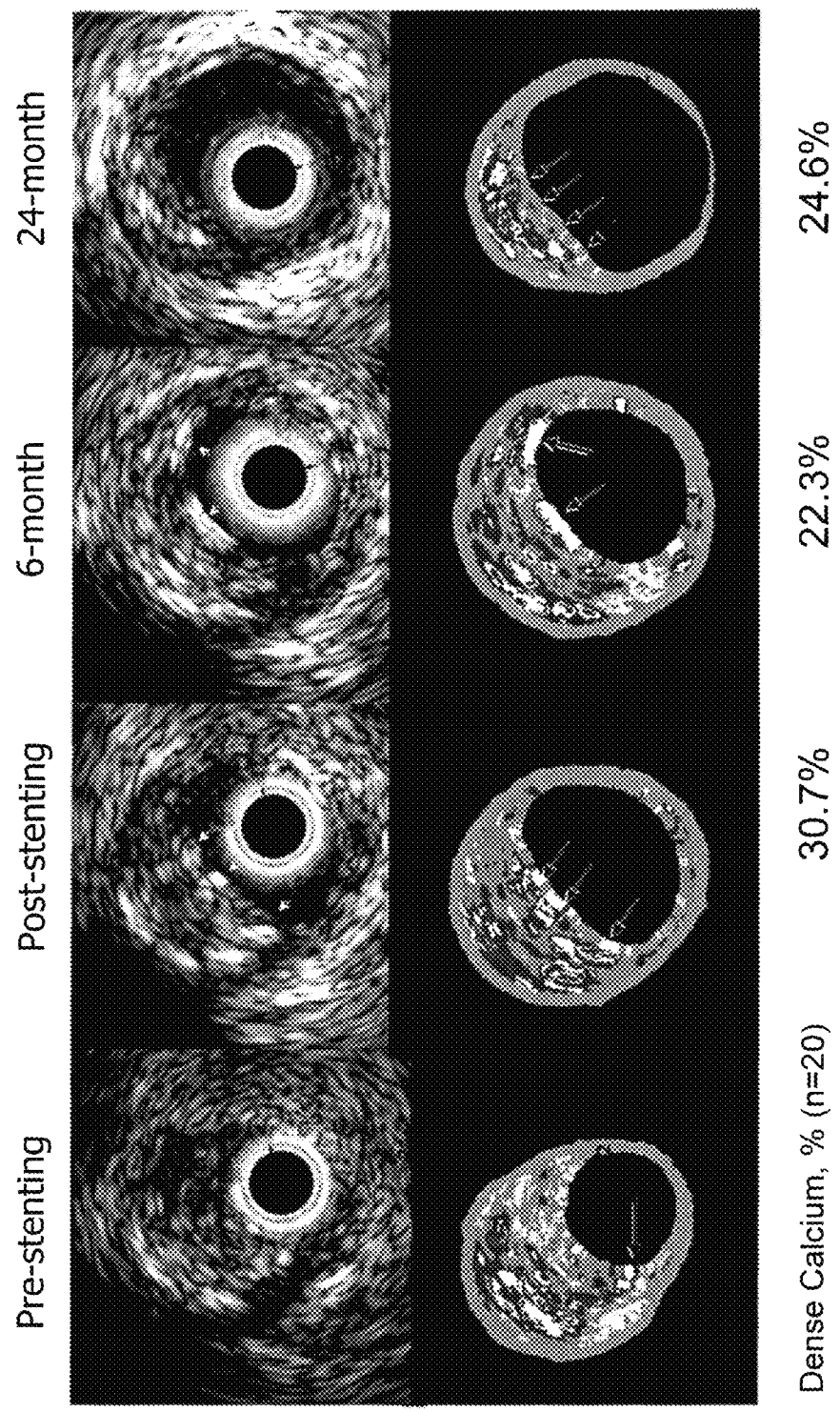
FIG. 10 depicts gray-scale IVUS-VH images and the corresponding radiofrequency processed images of a vessel of patient before stenting, post-stenting, 6 months after stenting, and 2 years after stenting.

The time-dependent behavior also includes the change in the plaque geometric morphology parameters and the composition with time. These changes are demonstrated by the clinical results presented herein. The time-dependence of plaque morphology parameters and composition have been demonstrated by clinical results presented herein, for example, as shown in FIG. 10.

The parameters include the ratio of the thickness of the fibrous cap to the necrotic core. The clinical results have shown a regression of necrotic core as the stent degrades. Specifically, a vessel wall can have a necrotic core component at pre- and post-implantation that is in contact with a blood-contacting surface of the vessel wall. As the stent degrades the necrotic core regresses from the surface and the fibrous component becomes positioned between the necrotic core component and the blood-contacting surface of the vessel wall. As a result, the unstable necrotic core component is no longer in contact with the blood-contacting surface.

Another time-dependent plaque morphology parameter is the area of the necrotic core component as a percentage of the total plaque area. The clinical results show that as the stent degrades the area of the necrotic core component as a percentage of the total plaque region area decreases.

Another time-dependent plaque morphology parameter is necrotic core component as a percentage of the plaque. The clinical results show that between implantation and when the stent is completely or substantially degraded away, the necrotic core component as a percentage of the plaque has decreased and the fibrous component as a percentage of the plaque has increased.

Another plaque morphological parameter that changes with time is the shape of the plaque region. The implantation of the stent results in a change in the shape of a plaque region which is more stable and less susceptible to rupture. When the stent is implanted, the plaque region is redistributed, resulting in a change in shape. In addition, the redistribution changes the shape of the plaque region. The pressure exerted by the stent on the plaque region and vessel wall changes the radius of curvature of the plaque region. In particular, the surface of the plaque region is flattened. In other words, the radius of curvature of the plaque region is increased by the deployment of the stent. The pre- and post-stenting IVUS-VH images shown in FIG. 10 demonstrate this change in shape. This flattened profile of the plaque region is more stable and less vulnerable to rupture since there is lower stress at the corners of the plaque. This lower stress makes the plaque less susceptible to rupture.

Additionally, the plaque properties change with time as the stent degrades which allows the plaque to maintain the more stable shape even after the stent degrades. Specifically, it is believed that the vessel wall, including the plaque region, undergoes remodeling as the stent degrades. Due to the remodeling, the flattened shape or increased radius of curvature is maintained, even after the radial strength of the stent declines and is no longer able to support the vessel walls. Furthermore, the flattened shape or increased radius of curvature is maintained after the stent loses mechanical integrity and even after the stent erodes away completely from the section of the vessel. The IVUS-VH results shown in FIG. 10 show that the flattened shape is maintained at 2 years, at which the stent is almost completely eroded away.

Stent outputs and design inputs result in the time dependent behavior of the luminal area and plaque morphology parameters. The time-dependent behavior of the luminal area arises from stent outputs including the mechanical integrity profile and the radial strength profile. The time-dependent plaque geometric morphology parameters are a result of the mechanical integrity profile, radial strength profile, stent design, erosion profile. The remodeling of the plaque region is provided by the stent outputs and design inputs as described for remodeling of the vessel wall.

Figure 22:
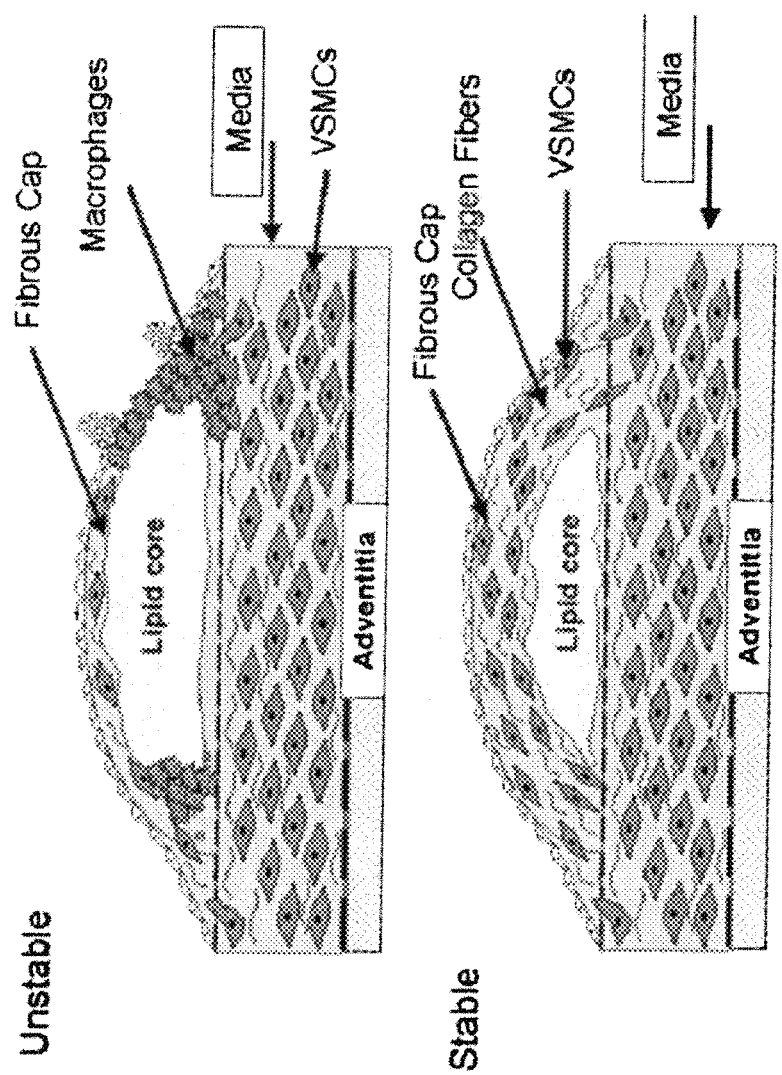
FIG. 22 is a schematic representation of the structure of vulnerable plaque.

The bioabsorbable stent of the present invention may be used to treat a section of a vessel having vulnerable plaque. A vulnerable plaque is an unstable collection of white blood cells (primarily macrophages) and lipids (including cholesterol) in the wall of an artery which is particularly prone to produce sudden major problems, such as a heart attack or stroke. Vulnerable plaque has a thin fibrous cap and a large and soft lipid pool underlying the cap. FIG. 22 is a schematic representation of the structure of vulnerable plaque. The upper panel shows the structure of unstable or vulnerable plaque. The fibrous cap is thin contains few VSMCs and collagen fibers. There are a large number of macrophages particularly at the shoulder region where the cap meets the healthy endothelium. There is a large lipid core. The lower panel shows a stable plaque with a thick fibrous cap and a small lipid core. There many VSMCs and collagen fibers. The characteristics of vulnerable plaque together with the usual hemodynamic pulsating expansion during systole and elastic recoil contraction during diastole contribute to a high mechanical stress zone on the fibrous cap of the atheroma, making it prone to rupture.

In such embodiments, the bioabsorbable stent may be deployed at a section of the blood vessel that has a vulnerable plaque region. The deployment of the stent would increase the radius of curvature of the vulnerable plaque region. It is expected that as the stent degrades the fibrous cap remodels and would be capable of maintaining an increased radius of curvature after radial strength of the stent declines and can no longer support the vessel walls. Additionally, it is expected that the fibrous cap could maintain the increased radius of curvature after the stent loses mechanical integrity and after the stent erodes away from the section of the vessel.

The stent for treating vulnerable plaque can be self-expanded or balloon expanded. The stent can include a soft or elastomeric outer layer on at least the surface that contacts the plaque region. This outer layer can act as a cushion to prevent rupture of the vulnerable plaque upon deployment of the stent. In addition, the deployment pressure of the balloon used to deploy the stent can be between 30 and 80 psi to prevent rupture of the vulnerable plaque.

The fabrication methods of a bioabsorbable stent for use in the methods of treatment described herein can include the following steps:

(1) forming a polymeric tube using extrusion,
(2) radially deforming the formed tube,
(3) forming a stent scaffolding from the deformed tube by laser machining a stent pattern in the deformed tube with an ultra-short pulse laser,
(4) forming a therapeutic coating over the scaffolding,
(5) crimping the stent over a delivery balloon, and
(6) sterilization with e-beam radiation.

The stent scaffolding is formed from a semicrystalline polymer. In particular, a semicrystalline polymer is selected that has a Tg that is greater than body temperature (about 37° C.) so that the scaffolding is in a rigid state after implantation which allows the scaffolding to provide support without excessive recoil.

As indicated above, the mechanical properties of a polymer can be modified by applying stress to a polymer. In particular, the strength of a polymer can be increased along the direction of the applied stress. Without being limited by theory, the application of stress induces molecular orientation along the direction of stress which increases the strength. Molecular orientation refers to the relative orientation of polymer chains along a longitudinal or covalent axis of the polymer chains.

The fabrication of the polymeric stent includes radially deforming an extruded polymeric tube about its cylindrical axis. Radial deformation increases the radial strength of the tubing, and the subsequently a stent fabricated from the deformed tube. The increase in strength is due to the induced polymer orientation in the circumferential direction. It has also been observed that the deformation increases the fracture toughness of a stent. Both the increase in radial strength and fracture toughness are important to the ability of the stent to heal a diseased segment of a blood vessel.

Additionally, the stent can have a biaxially oriented polymer structure. To achieve this, the tube is axially deformed to provide increased strength in the axial direction, in addition to being radially deformed. For example, the tube may be axially deformed by applying a tensile force to the tube along its cylindrical axis. In some instances, only sufficient tension is applied to maintain the length of the tube as it is expanded.

It is generally desirable to deform the tube at a temperature above the Tg of the polymer. For an exemplary polymer, PLLA, which has a Tg of about 60° C., the polymer can be heated to a temperature between 65-120° C. during deformation. Deforming at such low temperatures favors a high nucleation density and smaller crystals, which provides high fracture toughness. The high density of crystallites that are formed behave a crosslink points that inhibit crack formation and propagation.

Figure 6A:
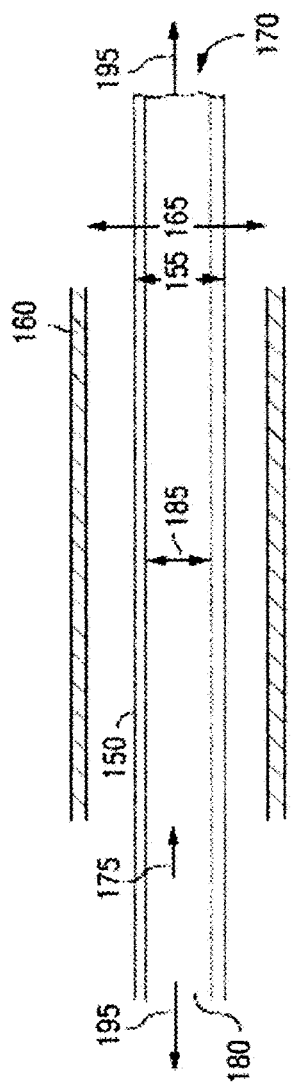
FIGS. 6A-B depict a blow molding process of a polymer tube.
Figure 6B:
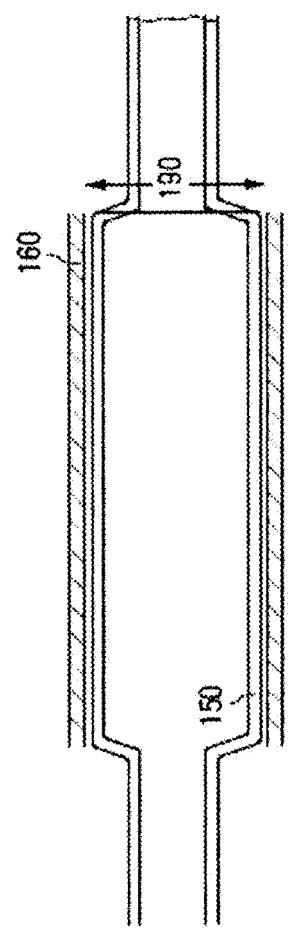

The polymeric tube is radially deformed using blow molding through the use of a balloon blower adapted to radially expand a polymer tube. FIGS. 6A-B illustrate an embodiment of deforming a polymeric tube. FIG. 6A depicts an axial cross-section of a polymeric tube 150 with an outside diameter 155 positioned within a mold 160. Mold 160 limits the radial deformation of polymeric tube 150 to a diameter 165, the inside diameter of mold 160. Polymer tube 150 may be closed at a distal end 170. Distal end 170 may be open in subsequent manufacturing steps. A fluid is conveyed, as indicated by an arrow 175, into an open proximal end 180 of polymeric tube 150 to increase the pressure inside of the tube. A tensile force 195 is applied at proximal end 180 and a distal end 170 to axially deform tube 150.

Polymeric tube 150 is heated by a nozzle directing a heated gas onto the mold surface. For example, the nozzle can heat the tube as it translates along the length of the tube. The increase in pressure inside of polymer tube 150 facilitated by an increase in temperature of the polymeric tube causes radial deformation of polymer tube 150 as the nozzle translates, as indicated by an arrow 185. FIG. 6B depicts polymeric tube 150 in a deformed state with an outside diameter 190 within annular member 160.

The tube is expanded to a target diameter. The stent pattern can be cut into the tube with laser machining at the target diameter. The target diameter can also correspond to the diameter of a stent prior to crimping.

The degree of radial deformation may be quantified by percent radial expansion:

$$\left[\frac{\text{Outside Diameter of Deformed Tube}}{\text{Original outside Diameter of Tube}} - 1\right] \times 100\%$$

In some embodiments, percent radial expansion can be 200-500%. In an exemplary embodiment, the percent radial expansion is about 300%. Similarly, the degree of axial deformation may be quantified by the percent axial elongation:

$$\left[\frac{\text{Length of Deformed Tube}}{\text{Original Length of Tube}} - 1\right] \times 100\%$$

The percent axial elongation can be 20-100%.

Axial polymer orientation is also imparted to a tube during formation of the tube as the polymer is drawn out of a die during the extrusion process. The degree of axial orientation of a polymer provided by the draw down process is related the axial drawn down ratio:

$$\frac{\text{Inside Diameter of Die}}{\text{Original Inside Diameter of Tube}}.$$

In an exemplary embodiment the axial drawn down ratio is 2:1 to 7:1.

The stent pattern is formed in the tube with an ultrashort-pulse laser. "Ultrashort-pulse lasers" refer to lasers having pulses with pulse durations shorter than about a picosecond ($=10^{-12}$). Ultrashort-pulse lasers can include both picosecond and femtosecond (=$10^{-15}$) lasers. The stent pattern is formed with a laser with a pulse width less than 200 fs. In an exemplary embodiment, the pulse width used is 120 fs. The use of a femtosecond laser reduces or eliminates damage to polymer material that is uncut and forms the structure of the stent scaffolding.

Figure 7:
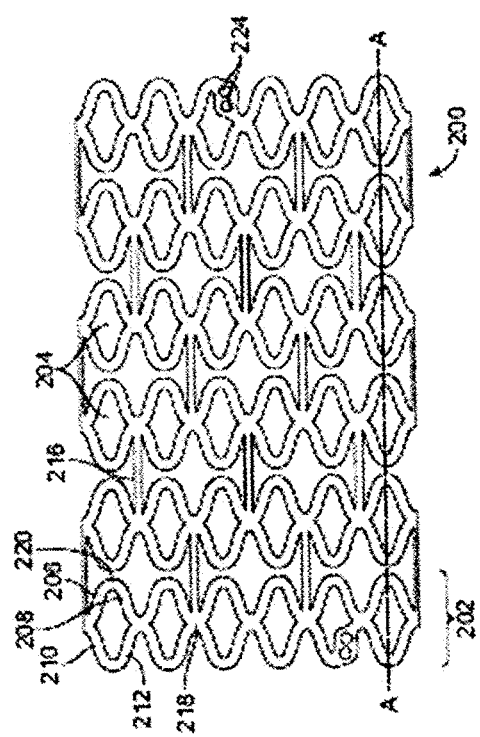
FIG. 7 depicts a stent pattern.

FIG. 7 depicts an exemplary stent pattern 200. Stent pattern 200 can be cut from a polymeric tube using the laser machining methods described above. Stent pattern 200 is shown in a flattened condition so that the pattern can be clearly viewed. When the flattened portion of stent pattern 200 is in a cylindrical form, it forms a radially expandable stent.

As depicted in FIG. 7, stent pattern 200 includes a plurality of cylindrical rings 202 with each ring made up of a plurality of diamond shaped cells 204. Stent pattern 200 can have any number of rings 202 depending a desired length of a stent. For reference, line A-A represents the longitudinal axis of a stent using the pattern depicted in FIG. 7. Diamond shaped cells 204 are made up of bar arms 206 and 208 that form a curved element and bar arms 210 and 212 that form an opposing curved element.

Pattern 200 further includes linking arms 216 that connect adjacent cylindrical rings. Linking arms 216 are parallel to line A-A and connect adjacent rings between intersection 218 of cylindrically adjacent diamond-shaped elements 204 of one ring and intersection 218 of cylindrically adjacent diamond shaped elements 204 of an adjacent ring. As shown, linking elements connect every other intersection along the circumference. Pattern 200 includes pairs of holes 224 in struts at both ends of the stent to accommodate radiopaque markers.

As discussed above, prior to delivery into the body a stent is compressed or crimped onto a catheter so that it can be inserted into small vessels. Once the stent is delivered to the treatment site, it can be expanded or deployed at a treatment site. Generally, stent crimping is the act of affixing the stent to the delivery catheter or delivery balloon so that it remains affixed to the catheter or balloon until the physician desires to deliver the stent at a treatment site. There are numerous crimpers available for crimping stents including, but not limited to, the roll crimper, collet crimper, and wedge crimper.

The bioabsorable stent is heated and crimped above ambient temperature. Heating a stent during crimping can reduce or eliminate radially outward recoiling of a crimped stent which can result in an unacceptable profile for delivery. In an exemplary embodiment, a bioabsorbable stent is crimped at a temperature between 25 and 50° C.

A crimping device can apply pressure and heat simultaneously. In these or other embodiments, after crimping, the crimping device can hold the stent at an elevated temperature, which may be selected such that it is greater than, equal to, or less than the selected crimping temperature or may be selected to specifically exclude temperatures greater than, equal to, or less than the selected crimping temperature. In some embodiments, the device crimps the polymeric stent while the stent is heated by other means.

The crimped stent is further packaged and sterilized. The stent is sterilized through exposure to an electron beam (e-beam). The range of exposure is between 25 and 30 kGy. The radiation exposure causes degradation in the polymer, particularly the molecular weight. As discussed above, the radial strength, mechanical integrity, and erosion profiles are influenced by the molecular weight. To reduce this degradation, the stent is sterilized after reducing its temperature below 0° C. by, for example, placing the stent in a freezer. Additionally, the initial molecular weight and dose are selected to obtain the necessary molecular weight for proper functioning of the stent.

For a stent with an exemplary PLLA scaffolding, the number average (Mn) and the weight average molecular weight (Mw) of the scaffolding before and after e-beam sterilization are given in Table 4.

TABLE 4

Molecular weight of resin and scaffolding.

| | Mn (kg/mol) | Mw (kg/mol) |
|---|---|---|
| PLLA Resin | 250-300 | 500-600 |
| PLLA scaffolding after e-beam | 80-100 | 150-200 |

The manufacturing process of a bioabsorbable polymer stent additionally described in U.S. patent application Ser. No. 11/443,94 which as been published as U.S. Patent Publication No. 20070283552, and is incorporated by reference herein.

EXAMPLES

Some embodiments of the present invention are illustrated by the following examples and clinical trial information. The examples and clinical trial information are being given by way of illustration only and not by way of limitation. The parameters and data are not be construed to unduly limit the scope of the embodiments of the invention.

Examples

Embodiments of a Stent can be Fabricated from Poly(L-Lactide) (PLLA)

Step 1: Tube Manufacturing

The resin for input into the extruder is granular. An exemplary PLLA resin has about a 70% crystallinity and Mn=265K, Mw=520K. Pre-extrusion processing includes baking in a vacuum oven that removes moisture and residual solvent, both of which can adversely affect the degradation profiles of the stent. For instance, moisture can accelerate degradation. The Tm of resin is about 176° C.

The resin is extruded in a 1" single screw extruder used to form tubing. The parameters are:

Extruded at 420 F+/−10 F (215° C.)
Residence time: approximately 10 min
Quenched in room temperature water bath
Die/quench distance is ¾"
Pull rate=16 ft/min
Barrel pressure=2000 psi
Draw down ratio approx 3:1 (ID die to ID of drawn tube)

The post-extrusion Mn=180 K, Mw=380K and crystallinity is 10-15%.

Step 2: Radial Expansion

The extruded tubing is expanded from 0.018 in inside diameter (ID)/0.056 in outside diameter (OD) to (0.065 in to 0.080 in ID)/(0.077 in to 0.092 in OD), with 30-80% longitudinal stretch of the tube. The tubing is expanded by blow molding in a glass mold. The degree of crystallinity after expansion can be between 30% and 55%. The temperature of the tube during radial expansion can be between 160° F. and 210° F.

Step 3: Laser Machining and Stent Pattern

Laser machining is performed with a laser having a 120 femtosecond pulse. The wavelength of the laser is 800 nm.

Stent struts can have a rectangular or square cross-section. For example, the struts can measure 0.0065×0.0065 in (150×150 micron).

Step 4: Crimping

The stent is crimped from the cut diameter to a desired diameter onto a support element, such as a balloon. A sliding wedge style crimper can be used. The crimp cycle may be between about 30 and 300 seconds. The stent can be heated to a temperature between 28° C. and 48° C. during crimping. The stent can be crimped from a 0.084 in OD to a 0.053 in OD.

Step 5: Sterilization

The stent is sterilized by e-beam sterilization with a range of exposure between 25 and 30 kGy.

Step 5: Deployment

The crimped stent can be deployed with an outward radial pressure in the balloon of 7 atm to 0.118 (3.0 mm) ID or a pressure of up to 16 atm to 0.138 in (3.5 mm) ID.

Clinical Trial Data

Clinical trials involving implantation of a bioabsorbable stent in 30 patients were performed. A bioasorbable everolimus-eluting stent system from BVS of Abbott Vascular, Santa Clara, Calif. referred to herein as "the BVS stent," was used in the study. The BVS stent system is made from a bioabsorbable poly(L-lactide) (PLLA) scaffolding or backbone which is coated with a more rapidly absorbing poly (D,L-lactide) (PDLLA) layer that contains and controls the release of the antiproliferative drug, Everolimus (Novartis, Basel, Switzerland). Clinical trial results up to 2 years follow-up are reported in., Lancet.com Vol. 373 Mar. 14, 2009, which is incorporated herein by reference.

The fabrication process of the BVS stent includes the steps described above, extrusion of a PLLA tube, radial and axial deformation of the tube, and laser machining a pattern. The PDLLA coating is applied to the machined backbone prior to crimping on a delivery balloon.

FIGS. 8A-B depict images of the BVS stent used in the studies and is the same as the pattern depicted in FIG. 7. FIG. 8B depicts a magnified image of the BVS stent. The stent has struts 150 μm thick either directly joined or linked by straight bridges. Both ends of the stent have two adjacent radiopaque metal markers. The markers at one end are shown in FIG. 8B. The BVS stent shown in FIGS. 8A-B has a backbone of PLLA coated with PDLLA. As mentioned above, PLLA is a semicrystalline polymer which is composed of crystalline regions with an amorphous matrix. The PDLLA in the coating is a random copolymer of D-lactide and L-lactide. The presence of the D-lactide segments inhibits crystallization, so the PDLLA is completely amorphous. At room and physiological temperatures, both PLLA and PDLLA are in the solid state and below their respective glass transition temperatures. The PDLLA coating contains and controls the release of the antiproliferative drug, everolimus. Both PLLA and PDLLA are fully bioabsorbable. During bioabsorption, the long chains of PLLA and PDLLA are progressively shortened as ester bonds between repeat units of lactide are hydrolyzed and small particles less than 2 μm in diameter are phagocytosed by macrophages. Ultimately, PLLA and PDLLA degrade to lactic acid, which is metabolized via the Krebs cycle.

The dose of everolimus on the BVS stent is 98 μg for a 12 mm stent (153 μg for the 18 mm stent). Within 28 days of implantation, 80% of the drug has eluted from the polymer coating.

Some design inputs of the stent are provided in Table 5.

TABLE 5

Summary of design inputs for BVS stent.

| Specification | Value |
| --- | --- |
| Backbone polymer (PLLA) | |
| Mw | 180,000-200,000 |
| Mn | 90,000-100,000 |
| Mass of stent (12 mm length) | 5.9 mg |
| Mass/unit length | 0.5 mg/mm |
| Crystallinity | 45% (as measured by DSC) |
| Strut cross section | 150 micron × 150 micron |
| Coating thickness | 2 microns |
| Coating mass | 196 μg (1:1 polymer:Everolimus) |
| Coating polymer | |
| Mw | 66,000 |
| Mn | 39,000 |
| Blow molding: | |
| Percent radial expansion | 300% |
| Percent axial elongation | 50% |
| Laser machining | 120 fs laser |

Clinical data up to two years has been obtained. The techniques and measurements include the following:

Quantitative coronary angiography (QCA) was used to analyze the stented segment and the peri-stent segments (defined by a length of 5 mm proximal and distal to the stent edge), as well as their combination (in-segment analysis);

QCA was used to study vasomotion at 2 years by measuring mean lumen diameter after administering either the endothelium independent vasoconstrictor methylergometrine maleate or the endothelium dependent vasoactive agent acetylcholine;

Phased array intravascular ultrasound catheters (IVUS) (EagleEye; Volcano Corporation, Rancho Cordova, Calif., USA) were used to examine stented vessel segments from after the procedure and from follow-up;

Optical coherence tomography (OCT) was used to study strut apposition and changes in strut appearance at intervention and at 6 months and 2 years after intervention.

Gray-scale IVUS images were used to assess appearance of polymer struts;

Gray-scale IVUS was used to assess echogenecity of polymer struts;

IVUS with virtual histology (IVUS-VH) (Volcano Corporation, Rancho Cordova, Calif., USA) using backscattering of radiofrequency signals was used to obtain information about tissue composition of the vessel wall;

Palpography based on IVUS was used to assess deformability of the vessel wall;

Multislice CT imaging was done 18 months to determine vessel dimensions;

The 30 patients had stable, unstable, or silent ischaemia and a single de-novo lesion that was suitable for treatment with a single 3.0×12 mm or 3.0×18 mm stent.

Some conclusions of analytical techniques are:

IVUS with echogenicity, IVUS with virtual histology, and OCT indicate that by 2 years, the BVS stent was incorporated into the vessel wall and bioabsorbed;

Reduction in molecular weight and mass had occurred to such an extent that struts were no longer recognizable by intravascular ultrasound, leaving behind few visible features, a third of stents were no longer discernible by OCT;

OCT showed an optically homogeneous vessel wall structure that, taken together with the documented restoration of vasomotion, suggests healing of the artery.

Figure 9:
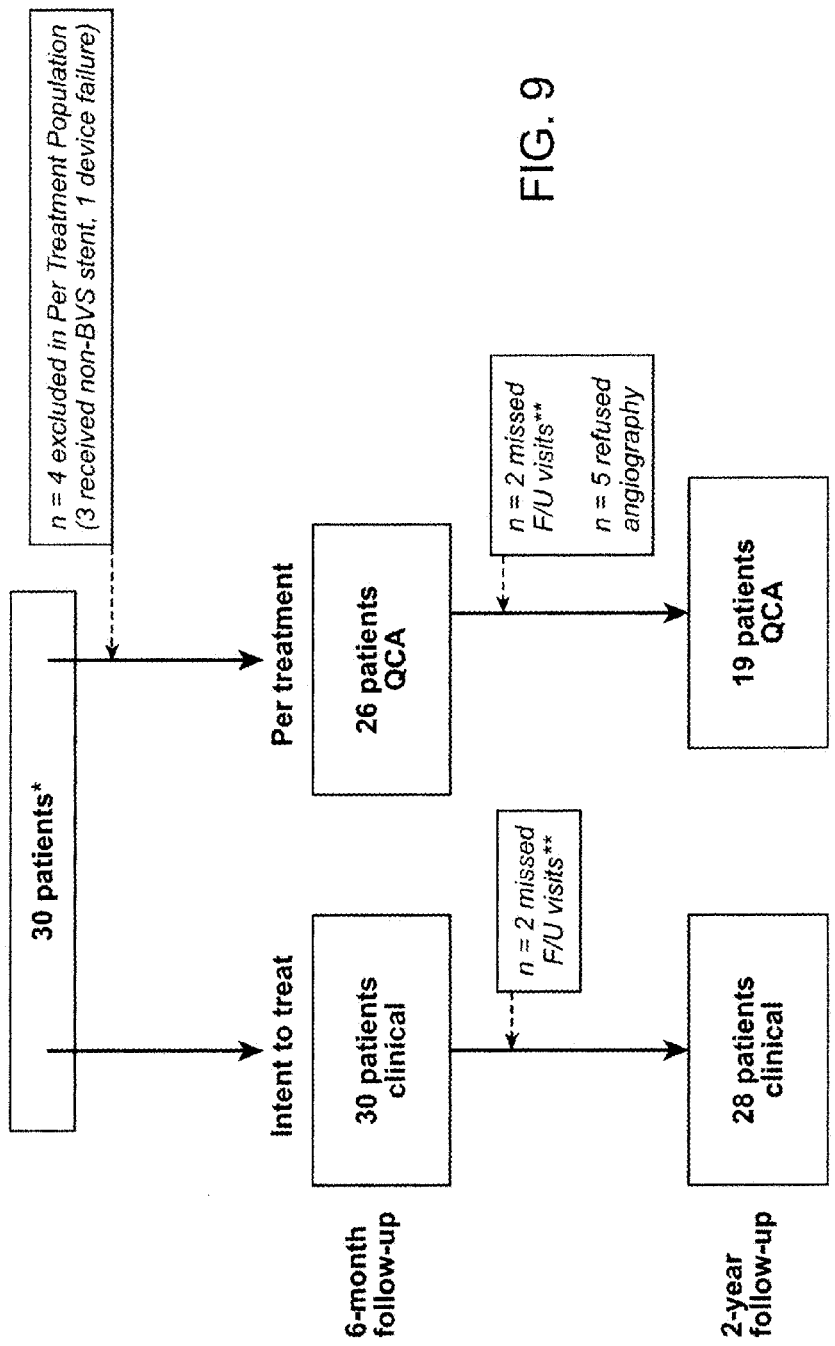
FIG. 9 is a flow chart that summarizes a population of a clinical study.

FIG. 9 is a flow chart that summarizes the clinical population. Four patients were excluded from the per treatment-evaluable population since they received a non-BVS stent in addition to the study stent (BVS). The per treatment-evaluable population was the primary population. Angiographic endpoints, intravascular ultrasound, and derived morphology parameters were assessed at 6 months (range 14 days) and at 2 years.

Published information regarding the clinical trials up to 6 months follow-up can be found in the following: Ormiston et al., Lancet.com Vol. 371 Mar. 15, 2008; Tanimoto, S. et al., J. of the American College of Cardiology, Vol. 52, No. 20, 2008; Ormiston, J. et al., Catheterization and Cardiovascular Interventions 69:128-131 (2007); Tanimoto, S. et al., Catheterization and Cardiovascular Interventions 70:515-523 (2007); all of which are incorporated by reference herein.

The clinical trials were a single-arm, prospective, open-label study. Patients were enrolled from four academic hospitals in Auckland, Rotterdam, Krakow, and Skejby. Patients were eligible if they were aged 18 years and older and had a diagnosis of stable, unstable, or silent ischaemia. Additional key eligibility criteria were the presence of a single, de-novo lesion in a native coronary artery, which was visually assessed to be less than 8 mm in length for the 12 mm stent, or less than 14 mm in length for the 18 mm stent. (18 mm stents were available later during the enrollment period and were received by only two patients.) The reference-vessel diameter of the target lesion was 3.0 mm and the stenosis diameter 50% or more and less than 100%, with a thrombolysis in myocardial infarction (TIMI) flow grade of more than 1.

Quantitative Coronary Angiography (QCA) Analysis of BVS Stent

In every patient, the stented segment and peri-stent segments (defined as 5 mm proximal and distal to the stent edge) were analyzed by QCA. The following parameters for QCA were computed: lesion length, minimal luminal diameter (MLD), reference vessel diameter (RVD), and were obtained by an interpolated method. Additionally, binary restenosis was computed and is defined in every segment (stent and peri-stent segment) as diameter stenosis (DS) of 50% or more at follow-up. Results are presented as paired matched angiographic views after procedure and at follow-up.

Table 6 gives baseline characteristics of the per treatment-evaluable population and intention-to-treat population including vessel parameters from QCA. Definitions of vessel characteristics determined from QCA are as follows:

Post-procedural or post-percutaneous coronary intervention (PCI) refers to a time point immediately after or almost immediately after stent deployment.

"In stent" refers to a stented segment of a vessel.

"Reference vessel diameter" (RVD) is the diameter of a vessel in areas adjacent to a diseased section of a vessel that appear either normal or only minimally diseased.

"Minimal lumen diameter" (MLD) is the diameter of a diseased section of a vessel at the site of maximal reduction in the diameter.

% "Diameter restenosis" (% DS) is the percent difference between the reference vessel diameter and the minimal lumen diameter: (RVD MLD)/RVD "Acute gain" is defined as the difference between pre- and postprocedural minimal lumen diameter.

"Late loss" is defined as the difference between minimal luminal diameter after the procedure or post-percutaneous coronary intervention (PCI) and minimal luminal diameter at follow-up.

"Pre-stenting" or "pre-implantation" refers to before implantation or deployment of the stent at a section of a blood vessel.

"Post-stenting" or "post-implantation" refers to a time shortly after implantation or deployment of the stent at a section of a blood vessel. Measurements designated post-implantation are made, for example, immediately after a stent is implanted in a patient or the same day of implantation.

TABLE 6

Baseline characteristics of the per treatment-evaluable population and intention-to-treat population.

| | Per treatment-evaluable population n = 26 | Intention-to-treat population n = 30 |
|---|---|---|
| Age (years) | 62 (9) | 62 (9) |
| Men | 15 (58%) | 18 (60%) |
| Current smokers | 6 (23%) | 6 (20%) |
| Diabetes | 1 (4%) | 1 (3%) |
| Hypertension needing drugs | 16 (62%) | 18 (60%) |
| Hyperlipidaemia needing drugs | 16 (62%) | 19 (63%) |
| Previous target vessel intervention | 2 (8%) | 3 (10%) |
| Previous myocardial infarction | 1 (4%) | 1 (3%) |
| Stable angina | 18 (69%) | 21 (70%) |
| Unstable angina | 7 (27%) | 8 (27%) |
| Silent ischaemia | 1 (4%) | 1 (3%) |
| Target vessel | | |
| Left anterior descending | 13 (50%) | 15 (47%) |
| Left circumflex | 6 (23%) | 9 (30%) |
| Right coronary artery | 7 (27%) | 7 (23%) |
| AHA/ACC* lesion classification | | |
| B1 | 17 (65%) | 18 (60%) |
| B2 | 9 (35%) | 12 (40%) |
| Mean diameter of reference vessel (mm) | 2 · 78 (0 · 47) | 2 · 72 (0 · 47) |
| Minimum luminal diameter (mm) | 1.10 (0 · 26) | 1.06 (0 · 26) |
| Diameter stenosis (%) | 59% (12) | 60% (11) |
| Lesion length (mm) | 8 · 66 (3 · 97) | 9 · 15 (3 · 99) |

Data are mean (SD—standard deviation) or number (%), unless otherwise indicated.
*AHA/ACC = American Heart Association/American College of Cardiology Table 7 shows results of the QCA for vessel parameters at post-PCI, and 6 months and 2 years follow-up (F/U). In-stent angiographic late loss was 0.48 mm (SD 0.28) at 2 years. The in-stent late loss is similar to that reported with polymeric paclitaxel-eluting metallic stents (0.39 mm) [Stone, G. W., et al., N Engl J Med 2004; 350: 221-31; Fajadet, J. et al., Circulation 2006; 114: 798-806] more than that with metallic everolimus-eluting stents (about 0.15 mm) [Grube, E. et al., Circulation 2004; 109: 2168-71; Costa, R A et al.], less than that with a polymeric zotarolimus-eluting stent (about 0.6 mm) [Meredith I. T., et al., EuroIntery 2005; 1: 157-64; Fajadet, J., et al.; Circulation 2006; 114: 798-806] and less than that with bare-metal stents (usually more than 0.8 mm) [Ormiston et al., Lancet.com Vol. 371 Mar. 15, 2008]. The reference diameter decreased significantly from after the procedure to 6-month and 2-year follow-up, with an average loss of about 0.3 mm (Table 7). The late loss in the BVS stent is mostly due to reduction in stent area, but also induces some intrastent neointima hyperplasia.

TABLE 7

Unpaired QCA results for BVS stent.

| | After procedure | 6 months | 2 years | Difference after procedure vs 6 months (95% CI) | Difference 6 months vs 2 years (95% CI) |
|---|---|---|---|---|---|
| QCA (unpaired) | | | | | |
| n | 26 | 26 | 19 | — | — |
| In-stent RVD (mm) | 2.79 (0.41) | 2.64 (0.44) | 2.43 (0.33) | −0.15 (−0.25 to −0.05) | −0.12 (−0.21 to −0.03) |
| In-stent MLD (mm) | 2.32 (0.31) | 1.89 (0.31) | 1.76 (0.35) | −0.43 (−0.58 to −0.28) | −0.08 (−0.19 to 0.04) |
| In-stent DS (%) | 16% (6) | 27% (14) | 27% (11) | 10.51% (5.11 to 15.92) | 0.58% (−3.57 to 4.72) |
| In-stent late loss (mm) | — | 0.43 (0.37) | 0.48 (0.28) | — | 0.08 (−0.04 to 0.19) |
| Proximal late loss (mm) | — | 0.23 (0.31) | 0.34 (0.33) | — | 0.11 (−0.01 to 0.23) |
| Distal late loss (mm) | — | 0.23 (0.27) | 0.36 (0.37) | — | 0.16 (0.04 to 0.29) |
| In-stent absolute minimal luminal area ED (mm2) | 4.81 (1.75) | 3.22 (1.93) | 2.68 (1.21) | −1.59 (−2.67 to −0.52) | −0.02 (−0.45 to 0.41) |
| In-stent minimal luminal cross sectional area VD (mm2) | 5.53 (2.11) | 3.86 (2.26) | 3.18 (1.55) | −1.67 (−2.92 to −0.42) | −0.15 (−0.79 to 0.49) |
| In-segment late loss (mm) | — | 0.35 (0.32) | 0.37 (0.27) | — | 0.07 (−0.06 to 0.20) |
| In-stent binary restenosis (%) | — | 7.7% (2/26) | 0 (0/19) | — | −5.3% (−25.2 to 13.8) |
| In-segment binary restenosis (%) | — | 7.7% (2/26) | 0 (0/19) | — | −5.3% (−25.2 to 13.8) |

| | Difference after procedure vs 2 years (95% CI) | p value after procedure vs 6 months | p value 6 months vs 2 years | p value after procedure vs 2 years |
|---|---|---|---|---|
| QCA (unpaired) | | | | |
| n | — | — | — | — |
| In-stent RVD (mm) | −0.29 (−0.40 to −0.19) | 0.0094 | 0.0058 | <0.0001 |
| In-stent MLD (mm) | −0.48 (−0.61 to −0.35) | <0.0001 | 0.23 | <0.0001 |
| In-stent DS (%) | 10.10% (4.58 to 15.62) | 0.0002 | 0.81 | 0.0021 |
| In-stent late loss (mm) | — | — | 0.233 | — |
| Proximal late loss (mm) | — | — | 0.0553 | — |
| Distal late loss (mm) | — | — | 0.0091 | — |
| In-stent absolute minimal luminal area ED (mm2) | −1.89 (−2.65 to −1.12) | 0.0002 | 0.93 | <0.0001 |
| In-stent minimal luminal cross sectional area VD (mm2) | −2.04 (−2.96 to −1.11) | <0.0001 | 0.73 | <0.0001 |
| In-segment late loss (mm) | — | — | 0.42 | — |

TABLE 7-continued

| Unpaired QCA results for BVS stent. | | | | |
|---|---|---|---|---|
| In-stent binary restenosis (%) | — | — | 1 | — |
| In-segment binary restenosis (%) | — | — | 1 | — |

As shown in Table 7, between 6 months and 2 years, there was no significant differences in in-stent minimal lumen diameter, percentage of diameter stenosis, and in-stent late loss. Therefore, the significant decrease in minimal lumen diameter, reference vessel diameter, and luminal area already recorded at 6 months, remained significant at 2 years. Table 7 shows distal segment late loss increased significantly at 6 months and 2 years.

Acute stent recoil measured by QCA immediately after stent deployment was slightly higher than that of a matched population with lesions, who were receiving an everolimus-eluting metallic stent of 3 mm in diameter. Tanimoto, S., et al., Cather Cardiovasc Intery 2007; 70: 515-23. The acute recoil is on average 6.9% for the BVS stent and 4.3% for the everolimus-eluting metallic stent. The acute recoil of BVS stent in vessels less than 3 mm is 8.4% and 11.8% in a calcified lesion.

Explain statement from Lancet paper—Data that shows this: Patency and absence of binary restenosis was established non-invasively, and subsequently confirmed by conventional angiography.

Quantitative IVUS Measurements of Vessel

Stented vessel segments after the procedure and at follow-up were examined with phased array intravascular ultrasound (IVUS) catheters (EagleEye, Volcano Corporation, Rancho Cordova, Calif., USA) with automated pullback at 0.5 mm per second. The region beginning 5 mm distal to and extending 5 mm proximal to the stented segment was examined. The vessel area and mean lumen area were measured with a computer-based contour detection program (Curad, version 3.1).

As shown in Table 8 and FIGS. 10 and 11 (described in more detail below), gray-scale IVUS showed significant crease in minimal luminal area and average luminal area and volume, together with a significant decrease in plaque area and volume between 6 months and 2 years. With the exception of the minimal luminal area, findings for vessel area, average luminal area, plaque area, and lumen area stenosis at 2 years did not differ significantly from the measurement taken immediately after the procedure (table 3). The vessel area and volume remained constant between the follow-ups, showing the absence of significant remodeling.

TABLE 8

| Clinical trial IVUS analysis. | | | | | |
|---|---|---|---|---|---|
| | After procedure | 6 months | 2 years | Difference after procedure vs 6 months (95% CI) | Difference 6 months vs 2 years (95% CI) |
| n | 25 | 25 | 19 | — | — |
| Vessel (EEM) area (mm2) | 13.9 (3.74)† | 13.79 (3.84) | 12.75 (3.43) | −0.06 (−0.49 to 0.37) | −0.19 (−0.98 to 0.59) |
| Vessel volume (mm3) | 173.17 (52.04)† | 187.65 (72.75) | 178.21 (64.63) ‡ | 12.29 (−4.11 to 28.69) | 1.01 (−27.27 to 29.30) |
| Average lumen area (mm2) | 6.04 (1.12) | 5.19 (1.33) | 5.47 (2.11) | −1.01 (−1.30 to −0.71) | 0.68 (0.04 to 1.32) |
| Lumen volume (mm3) | 78.23 (22.98) | 70.66 (26.88) | 77.60 (35.98) ‡ | −9.20 (−16.84 to −1.56) | 12.42 (−1.19 to 26.03) |
| Plaque area (mm2) | 7.44 (2.83)† | 8.60 (2.85) | 7.10 (2.02) | 0.93 (0.45 to 1.40) | −1.06 (−1.48 to −0.64) |
| Plaque volume (mm3) | 94.56 (35.43)† | 116.99 (48.96) | 98.75 (36.47)‡ | 21.11 (9.51 to 32.72) | −13.38 (−30.22 to 3.47) |
| Minimal lumen area (mm2) | 5.09 (1.02) | 3.92 (0.98) | 4.34 (1.74) | −1.26 (−1.55 to −0.96) | 0.76 (0.22 to 1.31) |
| Lumen area stenosis (%) | 15.83% (7.64) | 23.62% (10.25) | 20.38% (6.92) | 7.28% (3.54 to 11.02) | −4.12% (−8.30 to 0.07) |

TABLE 8-continued

Clinical trial IVUS analysis.

| | | | | | |
|---|---|---|---|---|---|
| Projected MLD (mm) | 2.28 (0.26) | 2.04 (0.26) | 2.17 (0.43) | −0.26 (−0.35 to −0.18) | 0.19 (0.06 to 0.33) |

| | Difference after procedure vs 2 years (95% CI) | p value after procedure vs 6 months | p value 6 months vs 2 years | p value after procedure vs 2 years |
|---|---|---|---|---|
| n | — | — | — | — |
| Vessel (EEM) area (mm2) | −0.21 (−1.21 to 0.78) | 0.98 | 0.24 | 0.68 |
| Vessel volume (mm3) | 4.36 (−22.03 to 30.76) | 0.21 | 0.86 | 0.71 |
| Average lumen area (mm2) | −0.40 (−1.18 to 0.38) | <0.0001 | 0.0174 | 0.12 |
| Lumen volume (mm3) | −1.33 (−16.29 to 13.62) | 0.0032 | 0.0443 | 0.97 |
| Plaque area (mm2) | 0.01 (−0.71 to 0.72) | <0.0001 | 0.0001 | 0.80 |
| Plaque volume (mm3) | 4.09 (−11.81 to 20.00) | <0.0001 | 0.0063 | 0.71 |
| Minimal lumen area (mm2) | −0.59 (−1.26 to 0.08) | <0.0001 | 0.0026 | 0.0323 |
| Lumen area stenosis (%) | 4.07% (−1.30 to 9.44) | 0.0009 | 0.0569 | 0.0799 |
| Projected MLD (mm) | −0.07 (−0.26 to 0.11) | <0.0001 | 0.0052 | 0.23 | p-values per Wilcoxon's signed rank test

Serial Assessment of IVUS-VH Results

FIG. 10 and Table 9 provide serial assessments of IVUS-VH. FIG. 10 depicts gray-scale IVUS-VH images (top) and corresponding radiofrequency processed images (bottom) of a vessel of a patient before stenting, post-stenting, 6 months after stenting, and 2 years after stenting.

TABLE 9

Quantitative IVUS-VH results.

| | After procedure | 6 months | 2 years | Difference after procedure vs 6 months (95% CI) | Difference 6 months vs 2 years (95% CI) |
|---|---|---|---|---|---|
| IVUS virtual histology (unpaired)§ | | | | | |
| n | 25 | 25 | 18 | — | — |
| Dense calcium (%) | 29.82% (15.57) | 20.65% (11.50) | 26.42% (15.76) | −8.93% (−13.64 to −4.22) | 2.81% (−4.08 to 9.70) |
| Dense calcium area (mm2) | 1.02 (0.58) | 0.94 (0.64) | 0.81 (0.67) | −0.11 (−0.36 to 0.15) | −0.11 (−0.40 to 0.17) |
| Fibro-fatty tissue (%) | 4.31% (3.35) | 7.19% (6.17) | 5.47% (5.22) | 2.94% (0.40 to 5.48) | −0.41% (−3.50 to 2.67) |

TABLE 9-continued

Quantitative IVUS-VH results.

| | | | | |
|---|---|---|---|---|
| Fibro-fatty area (mm2) 0.21 (0.22) | 0.40 (0.43) | 0.19 (0.24) | 0.19 (0.02 to 0.35) | −0.12 (−0.27 to 0.04) |
| Fibrous (%) 38.83% (13.41) | 50.54% (12.69) | 43.66% (14.69) | 11.79% (6.84 to 16.74) | −3.38% (−10.59 to 3.82) |
| Fibrous area (mm2) 1.72 (1.22) | 2.62 (1.44) | 1.35 (0.92) | 0.80 (0.51 to 1.10) | −0.92 (−1.25 to −0.58) |
| Necrotic core (%) 27.04% (7.00) | 21.62% (8.70) | 24.45% (6.84) | −5.79% (−9.45 to −2.13) | 0.99% (−2.48 to 4.46) |
| Necrotic core area (mm2) 1.17 (0.82) | 1.13 (0.87) | 0.79 (0.51) | −0.13 (−0.38 to 0.11) | −0.26 (−0.53 to −0.00) |

| | Difference after procedure vs 2 years (95% CI) | p value after procedure vs 6 months | p value 6 months vs 2 years | p value after procedure vs 2 years |
|---|---|---|---|---|
| IVUS virtual histology (unpaired)§ | | | | |
| n 25 | — | — | — | — |
| Dense calcium (%) 29.82% (15.57) | −5.87% (−13.84 to 2.11) | 0.0003 | 0.64 | 0.21 |
| Dense calcium area (mm2) 1.02 (0.58) | −0.16 (−0.45 to 0.13) | 0.5046 | 0.31 | 0.21 |
| Fibro-fatty tissue (%) 4.31% (3.35) | 1.72% (−0.09 to 3.53) | 0.0142 | 0.85 | 0.21 |
| Fibro-fatty area (mm2) 0.21 (0.22) | 0.01 (−0.05 to 0.07) | 0.0096 | 0.0267 | 0.80 |
| Fibrous (%) 38.83% (13.41) | 6.75% (−0.68 to 14.17) | <0.0001 | 0.35 | 0.20 |
| Fibrous area (mm2) 1.72 (1.22) | −0.25 (−0.61 to 0.10) | <0.0001 | <0.0001 | 0.25 |
| Necrotic core (%) 27.04% (7.00) | −2.60% (−5.83 to 0.63) | 0.0028 | 0.64 | 0.30 |
| Necrotic core area (mm2) 1.17 (0.82) | −0.28 (−0.50 to −0.05) | 0.342 | 0.1089 | 0.0268 |

Backscattering of radiofrequency signals provides information about tissue composition of the vessel wall (with use of IVUS-VH). In the radiofrequency processed images, typically the necrotic core is represented as red areas on ultrasound cross-sections, dense calcium as white, fibro-fatty tissue as yellow-green, and fibrous tissue as green, and expressed as percentages (per cross-section, with the total equaling 100%). On every cross-section, polymeric stent struts were detected as areas of apparent dense calcium due to the strong backscattering properties of the polymer.

The change in quantitative analysis of these areas between implantation and follow-up is used as a surrogate assessment of the polymer bioabsorption process. Therefore, a substantial portion of the 29.82% at post-stenting measured as dense calcium is polymeric stent struts. The white areas in the post-stenting radiofrequency images of FIG. 10 represent the stent struts. At 6 month follow-up, the dense calcium measurement has decreased to 20.65%, indicating that the struts are partially absorbed at this time point. The lumen area is shown in each radiofrequency image.

As shown, the lumen area increases from 3.9 mm$^2$ at pre-stenting to 7.1 mm$^2$ at post-stenting, illustrating the enlargement of the lumen by the stent deployment. The increase in lumen diameter is apparent. Although there is a slight decrease in lumen area to 6.9 mm$^2$ at 6 months follow-up, the lumen size is maintained with no apparent restenosis. At 2 years follow up, the lumen areas has increased to 10.1 mm$^2$ and the lumen size is maintained.

From the OCT measurements discussed below, the stent is completely or almost completely absorbed at 2 year follow-up. Thus, the slight increase in the dense calcium measurement of 26.42% at 2 year follow-up in Table 9 is not a measurement of polymer strut, rather it is likely a measurement of calcification of the void left by the absorbed stent strut.

The IVUS-VH assessments showed that the percentage of each plaque component did not differ significantly between 6 months and 2 years (Table 9, FIG. 10). The absolute fibro-fatty area and fibrous-plaque area decreased significantly between 6 months and 2 years (Table 9). When compared with measurements taken immediately after the procedure, none of the 2-year parameters differed significantly, apart from necrotic core area (Table 9).

A shown in the lower three panels of FIG. 10, at pre-stenting there is a large plaque with a necrotic core. The arrow in the pre-stenting frame indicates the necrotic core is in contact with the lumen. After stenting, the lumen has enlarged to 7.1 mm$^2$ and two arrows point at two struts that are depicted as (pseudo) dense calcium. At 6 months, the two struts remained visible as indicated by the arrows with partial reduction of the luminal area. At 2 years, the endoluminal pseudo-dense calcium depicting struts has disappeared, which is consistent with strut absorption. There is now a fibrous cap covering the necrotic core, as indicated by the arrows, and late enlargement of the lumen (10.1 mm$^2$) and shrinkage of the plaque.

IVUS: Tissue Echogenicity and Palpography

Figure 11:
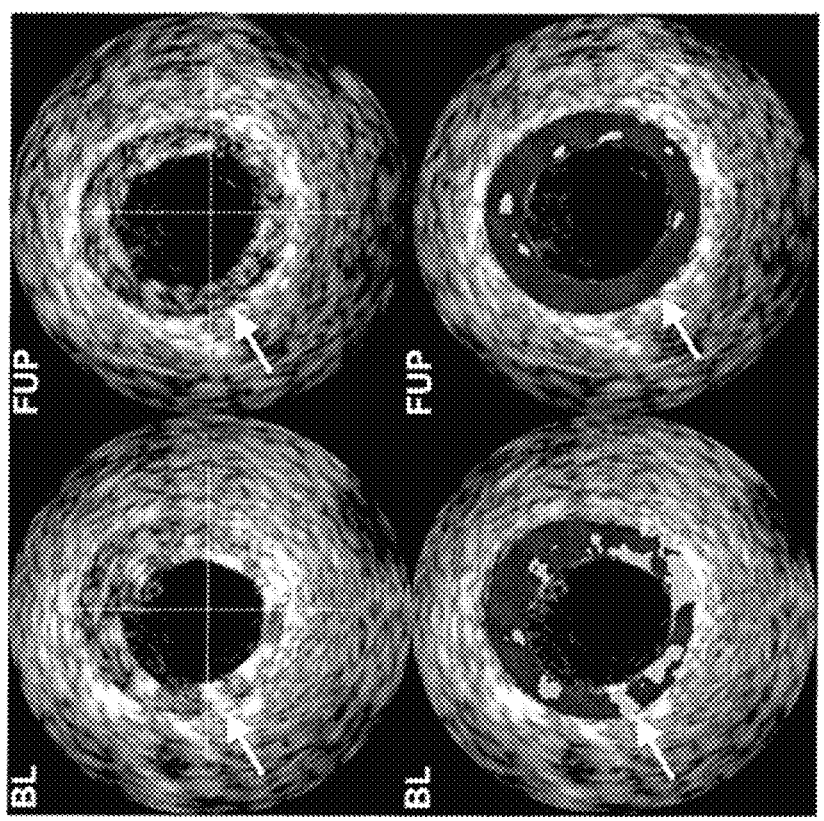
FIG. 11 depicts IVUS images with tissue echogenicity that are two-dimensional slices of an implant site of a single patient at post-PCI and at 6 months follow-up.

FIG. 11 depicts IVUS images with tissue echogenicity of two-dimensional radial slices of an implant site of a single patient at post-PCI and at 6 months follow-up. Table 10 and FIG. 11 show that a significant reduction in percentage of hyperechogenic tissue between after the procedure and at 6 months, and between 6 months and 2 years, in the intention-to-treat population was detected. The residual level of hyperechogenicity at 2 years as similar to the natural hyperechogenicity of plaques (7.7% [SD 6.5] vs 5.6% [4.8], n=12) that vas measured in one investigating center (Thorax Center, Rotterdam, Netherlands). Importantly, persistent and late acquired incomplete apposition detected at 6 months and previously repotted, 6 were no longer detectable at 2-year follow-up.

TABLE 10

Tissue echogenicity and palpography results.

| | After procedure | 6 months | 2 years | Difference after procedure vs 6 months (95% CI) | Difference 6 months vs 2 years (95% CI) |
|---|---|---|---|---|---|
| Palpography (unpaired) | | | | | |
| n | 24 | 23 | 17 | — | — |
| Strain values | 0.16 (0.10) | 0.28 (0.12) | 0.31 (0.17) | 0.12 (0.06 to 0.17) | 0.02 (−0.05 to 0.08) |
| Echogenicity (ITT) | | | | | |
| n | 27 | 26 | 21 | — | — |
| Hyperechogenicity (%) | 18.5% (9.1) | 10.3% (7.6) | 7.7% (6.5) | −8.15% (−11.00 to −5.31) | −3.75% (−62.0 to −1.29) |

| | Difference after procedure vs 2 years (95% CI) | p value after procedure vs 6 months | p value 6 months vs 2 years | p value after procedure vs 2 years |
|---|---|---|---|---|
| Palpography (unpaired) | | | | |
| n | — | — | — | — |
| Strain values | 0.13 (0.06 to 0.21) | 0.0002 | 0.81 | 0.0052 |
| Echogenicity (ITT) | | | | |
| n | — | — | — | — |
| Hyperechogenicity (%) | −12.81% (−16.19 to −9.44) | <0.0001 | 0.001 | <0.0001 |

In FIG. 11, the two top images are gray-scale IVUS images at post-PCI and 6 months follow-up, respectively. The bottom images are color-coded echogenicity images at post-PCI and 6 months follow-up, respectively. The green or lighter-colored portions are hyperechogenic material that correspond to stent struts. The red or darker areas are hypoechogenic tissue components that do not include stent struts. At 6 months follow-up, the images show that the stent struts are less pronounced, indicating absorption of stent struts at this time point.

Figure 12:
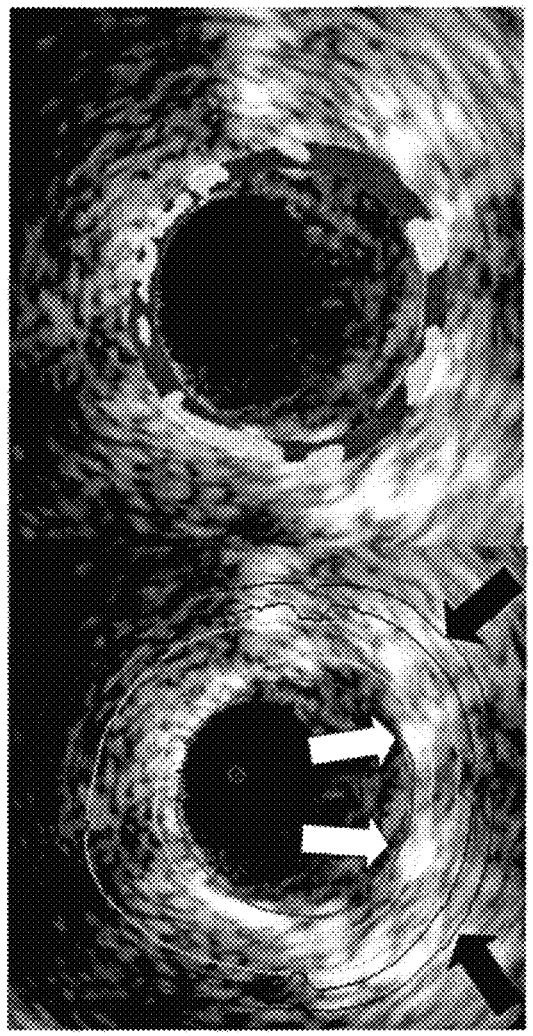
FIG. 12 depicts IVUS three-dimensional images with tissue echogenicity at post-PCI and at 6 months follow-up.

FIG. 12 depicts IVUS three-dimensional images with tissue echogenicity containing information along the entire axis of the stented site at post-PCI (left) and at 6 months follow-up (right). These images further illustrate the extent of absorption of the struts at 6 months follow-up.

In the palpography assessments, the underlying principle is that softer tissue is more readily deformed than is harder or scaffolded tissue when force (e.g., pulsatile arterial pressure) is applied. The rationale of this analysis for the study was to detect some subtle changes in strain resulting from scaffolding and late bioabsorption of the stent. The deformability of vessel wall was quantified with the analysis of back-scattering radiofrequency signals at different diastolic pressure levels.

Table 10 shows that the cumulative strain value increased significantly from after the procedure to 6-month follow-up, with no subsequent changes between 6 months and 2 years. The vessel wall deformability reappears to some extent in the initial 6 months and remained stable.

Quantitative OCT Measurements of Vessel

A commercially available OCT system was used in a subgroup of patients. This technique, with use of an infrared light source, has a resolution of 15 µm which is about ten times higher than that of intravascular ultrasound and therefore allows visualization of intracoronary structures in great detail. The light source is a 1310 nm broadband super luminescent diode with an imaging depth of about 1.5 mm, an axial resolution of 15 µm, and a lateral resolution of 25 µm. The imaging probe (ImageWire LightLab Imaging Inc, Westford, Mass., USA) has a maximum outer diameter of 0.4826 mm (0.019") and contains a 0.1524 mm (0.006") fiber-optic imaging core and a distal radiopaque spring tip, which is similar to conventional guide wires. An OCT catheter (Helios proximal occlusion catheter) is initially advanced distal to the area of interest over a conventional coronary guide wire, which is then replaced with the OCT imaging wire (ImageWire).

OCT data for the stent length, lumen area, minimal lumen area (MLA), minimal lumen diameter (MLD), and lumen volume are shown in Table 11 for PCI, 6 months follow-up, and 2 years follow-up. OCT data show a decrease in lumen area mean, MLA, and MLD at 6 months follow-up. Between 6 months and 2 years, there is an increase in mean and minimal lumen area and luminal volume.

Several explanations for the discordant late luminal changes between angiography and intracoronary imaging have been considered. Lancet.com Vol. 373 Mar. 14, 2009, p. 907.

Stent Strut Apposition and Appearance from OCT

The appearance of struts from OCT images changes at follow-up. The strut appearance can be characterized into four groups:

A "preserved box" has sharp defined, bright reflection borders with preserved box shaped appearance. The strut body shows low reflection. A preserved box is an image of a strut which has undergone little or no change.

An "open box" has luminal and abluminal "long-axis" borders thickened and bright reflection. "Short axis" borders are not visible. An open box is an image of a strut which has partially started to be dissolved.

A "dissolved bright box" is a partially visible bright spot with contours poorly defined and no box shaped appearance. A dissolved bright box is an image of a strut that has mostly dissolved.

A "dissolved black box" is a black spot with contours poorly defined and often confluent and no box shaped appearance. A dissolved black box is an image of a strut that has mostly dissolved and all or part of the void replaced by inorganic material.

Seven patients had serial data for OCT immediately after the procedure, at 6 months, and at 2 years (intention-to-treat population). The number of apparent struts decreased from 403 at baseline to 368 at 6-month follow-up and to 264 at 2

TABLE 11

Clinical trial OCT analysis.

| | After procedure | 6 months | 2 years | Difference after procedure vs 6 months (95% I) | Difference 6 months vs 2 years (95% CI) | Difference after procedure vs 2 years (95% CI) | p value after procedure vs 6 months | p value 6 months vs 2 years | p value after procedure vs 2 years |
|---|---|---|---|---|---|---|---|---|---|
| | | | | Optical CT (serial) | | | | | |
| n | 7 | 7 | 7 | — | — | — | — | — | — |
| Discernible struts | 403 | 368 | 264 | — | — | — | — | — | — |
| Mean lumen area (mm2) | 6.53 (0.91) | 4.72 (1.13) | 5.80 (2.93) | −1.81 (−3.39 to −0.23) | 1.08 (−0.93 to 3.08) | −0.74 (−3.42 to 1.94) | 0.0313 | 0.22 | 0.38 |
| Minimal lumen area (mm2) | 4.50 (1.03) | 2.65 (1.49) | 3.80 (2.42) | −1.84 (−3.48 to −0.21) | 1.15 (−0.14 to 2.43) | −0.7 (−2.62 to 1.22) | 0.0156 | 0.0781 | 0.47 |
| Mean lumen diameter (mm) | 2.87 (0.21) | 2.41 (0.31) | 2.63 (0.61) | −0.46 (−0.87 to −0.05) | 0.23 (−0.17 to 0.62) | −0.23 (−0.79 to 0.33) | 0.0313 | 0.22 | 0.30 |
| Lumen volume (mm3) | 84.1 | 58.0 | 74.1 | | | | | | |
| Stent length (mm) | 12.7 | 12.5 | 12.7 | | | | | | |

OCT imaging data (discussed below) show absorption of the stent into artery walls and that the blood vessel lining of arteries treated with the stent looks more uniform after two years than it did immediately post-treatment.

The significant increase in the average luminal area and minimal luminal area measured by WUS and OCT be veer 6 months and 2 years contrasts with the nonsignificant decrease in angiographic luminal dimensions during that period.

years (34.5% reduction over 2 years. For preserved box, appearance of stent strut changed from n=0 at 6 months to n=9 at 2 years, for open box from n=143 to n=68, for dissolved bright box from n=225 to n=185, and for dissolved black box from n=56 to n=25.

FIGS. 13A-B depicts serial assessment of stent struts by OCT. FIG. 13A shows, after stenting, incomplete apposition of struts (preserved box) in front of a side-branch ostium. At 6 months, persistent incomplete stent apposition (arrow) and resolved incomplete stent apposition (arrowhead), open box appearance. At 2 years, there is now smooth appearance of the endoluminal lining without strut malapposition since struts have been absorbed. There is guidewire shadowing (at the top of the image), and a strut is still just discernible as a bright spot (arrow).

In FIG. 13B, complete apposition of strut (box appearance) after the procedure is shown. At 6 months, there is late acquired incomplete stent apposition of the struts (preserved box appearance) with tissue bridging connecting the struts (arrow). The endoluminal lining is corrugated. At 2 years, the smooth endothelial lining with almost circular cross section. Generally, the struts are no longer discernible, although there is a bright reflection that could indicate a strut (arrow). Asterisk indicates a side branch.

All apparent struts were well covered and apposed to the vessel wall. All incomplete appositions (incomplete, persistent, and late acquired incomplete stent apposition) were resolved. The lumen shape was regular with smooth, well delineated borders in all cases, and we recorded no intraluminal tissue. The coronary vessel wall showed a homogenous, bright backscattering appearance, with no signs of tissue optical heterogeneity.

FIGS. 14A-D depict exemplary OCT images at 6 months follow-up of a preserved box, open box, bright dissolved box, and black dissolved box, respectively. At 6 months follow-up, 18 (3%) of 671 struts had a preserved box, 203 (30%) had an open box, 332 (50%) had a dissolved bright box, and 118 (18%) had a dissolved black-box appearance.

Figure 14A:
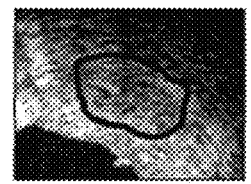
FIGS. 14A-D depict exemplary OCT images of sections of a treated vessel at six months follow-up which have undergone different-degrees of absorption.
Figure 14B:
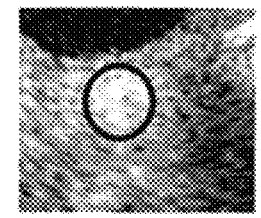
Figure 14C:
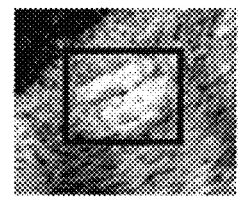
Figure 14D:
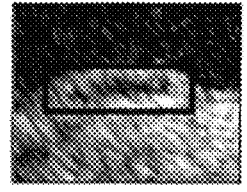

FIGS. 14C-D indicate that the stent has started to erode at 6 months, which means that the stent has started to lose mechanical integrity. The erosion and loss of mechanical integrity suggests that the stent has lost radial strength well before 6 months. If the stent had maintained mechanical integrity, all regions would look like FIG. 14A.

Figures 15A, 15B, 15C:
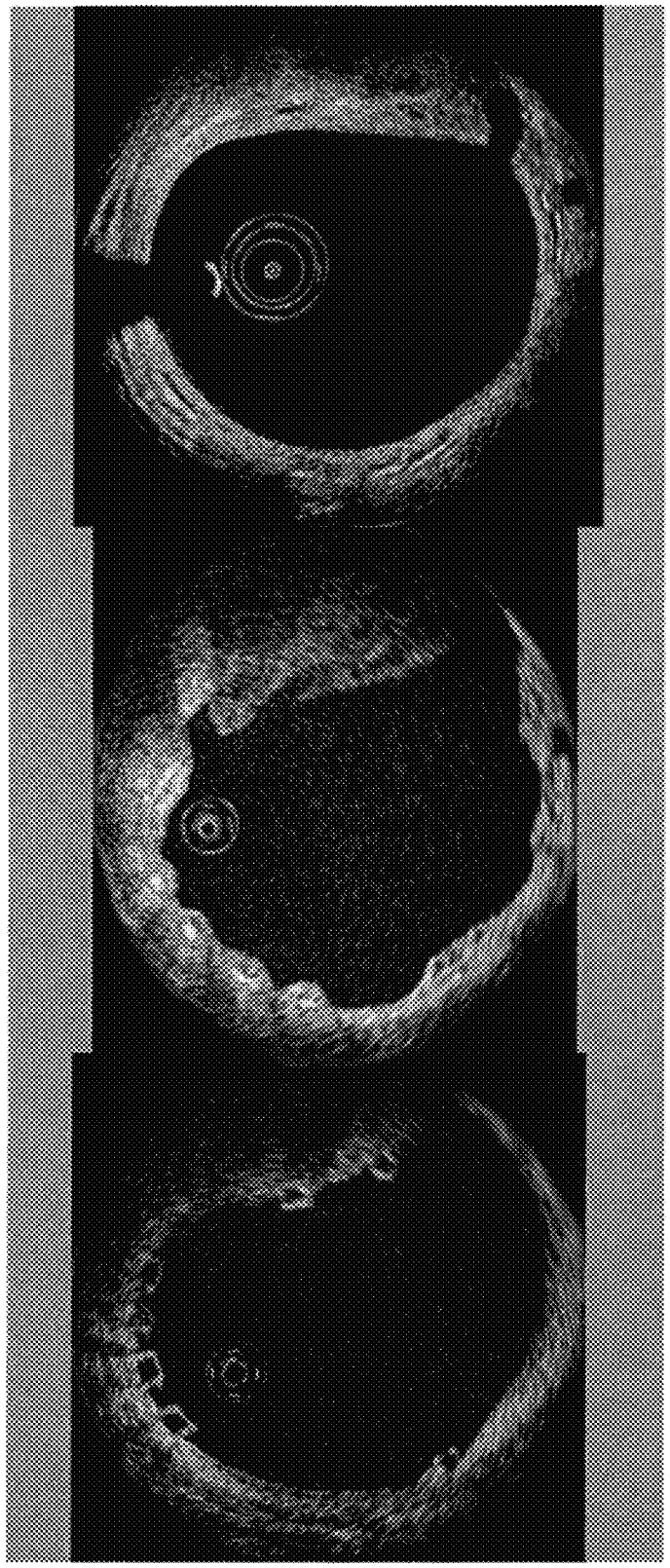
FIGS. 15A-C depict OCT images of a treated vessel post-PCT, at 6 months follow-up, and 2 years follow-up, respectively.
Figure 19B:
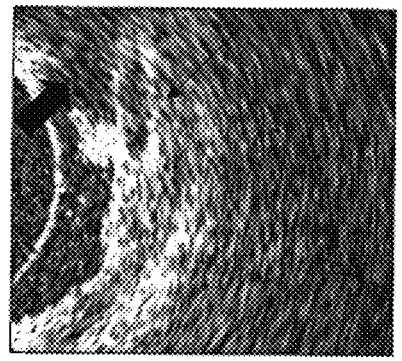
FIG. 19B depicts an OCT image of a section of a treated vessel in which arrows indicate incomplete tissue coverage of a strut.
Figure 19A:
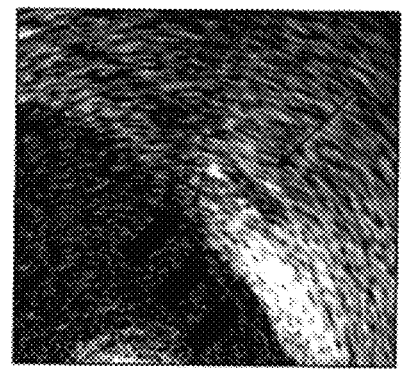
FIG. 19A depicts an OCT image of a section of a treated vessel in which arrows indicate complete tissue coverage of a strut.

FIGS. 15A-C depict complete OCT images post-PCI, at 6 months follow-up, and 2 years follow-up, respectively. The dark rectangular areas indicated in FIG. 15A correspond to the struts of the stent. In FIG. 15B, the dark areas are replaced by bright areas which indicate partially dissolved struts. No struts are apparent in FIG. 15C which suggest that the struts are almost or completely dissolved.

Bioabsorption as Shown by IVUS, IVUS-VH, and OCT for 2 Years Follow-Up

FIGS. 16A-B, 17A-B, and 18A-B are IVUS IVUS-VH, and OCT images, respectively, for one patient post-PCI and at 2 years follow-up. The top three frames from left to right, 15A, 16A, and 17A, are IVUS, VH, and OCT images post-PCI. The bottom three frames from left to right, 16B, 17B, and 18B, are IVUS, VH, and OCT images at 2 years.

In FIG. 16A, the white spots on the inner side of the vessel that are indicated correspond to stent struts. As shown in FIG. 16B, the whites spots are not present at 2 years follow-up.

In FIG. 17A-B, the white spots correspond to high density material and the stent struts are apparent around the vessel as indicated. As shown in FIG. 17B, after 2 years most of the stent struts have disappeared. The two white spots indicated may not be stent struts, but may be mineralization.

In FIG. 18A, black spots as indicated are stent struts that are in the inner side of the vessel. As shown in FIG. 18B, the black spots are replaced by bright yellow regions, as indicated, which indicates that stent struts are gone.

Endothelialization

Tissue coverage was present in 664 (99%) of the struts seen with an OCT image of a patient at 6 months (only seven had no tissue coverage as detected by OCT). FIG. 18A depicts an OCT image of a section in which arrows indicate complete tissue coverage of a strut. FIG. 18B depicts an OCT section in which arrows indicate incomplete tissue coverage of a strut.

Restoration of Vasomotion

Previously stented portion of arteries demonstrated the ability to expand and contract in a manner similar to a vessel that has never been stented. To study vasomotion at 2 years, either the endothelium independent vasoconstrictor methylergometrine maleate (methergin, Novartis, Basel, Switzerland), or the endothelium dependent vasoactive agent acetylcholine (Ovisot, Daiichi-Sankyo, Tokyo, Japan) was given. Potential restoration of unstented artery movement to coronary blood vessel after the bioabsorbable stent was absorbed was revealed at two years with the drugs acetylcholine and nitroglycerin used in nine patients and methergine in seven patients. Acetylcholine and nitroglycerin tend to induce vasodilation and methergine tends to induce vasoconstriction in blood vessels.

A method of subsegmental analysis was used to calculate the mean lumen diameter for the stented segment and its adjacent segments 5 mm proximally and distally. Each segment was divided into several subsegments and a mean lumen diameter of each segment was calculated from the subsegments. Measurements of the luminal diameter are shown for the stented segment, proximal segment, and the distal segment.

Figure 20A:
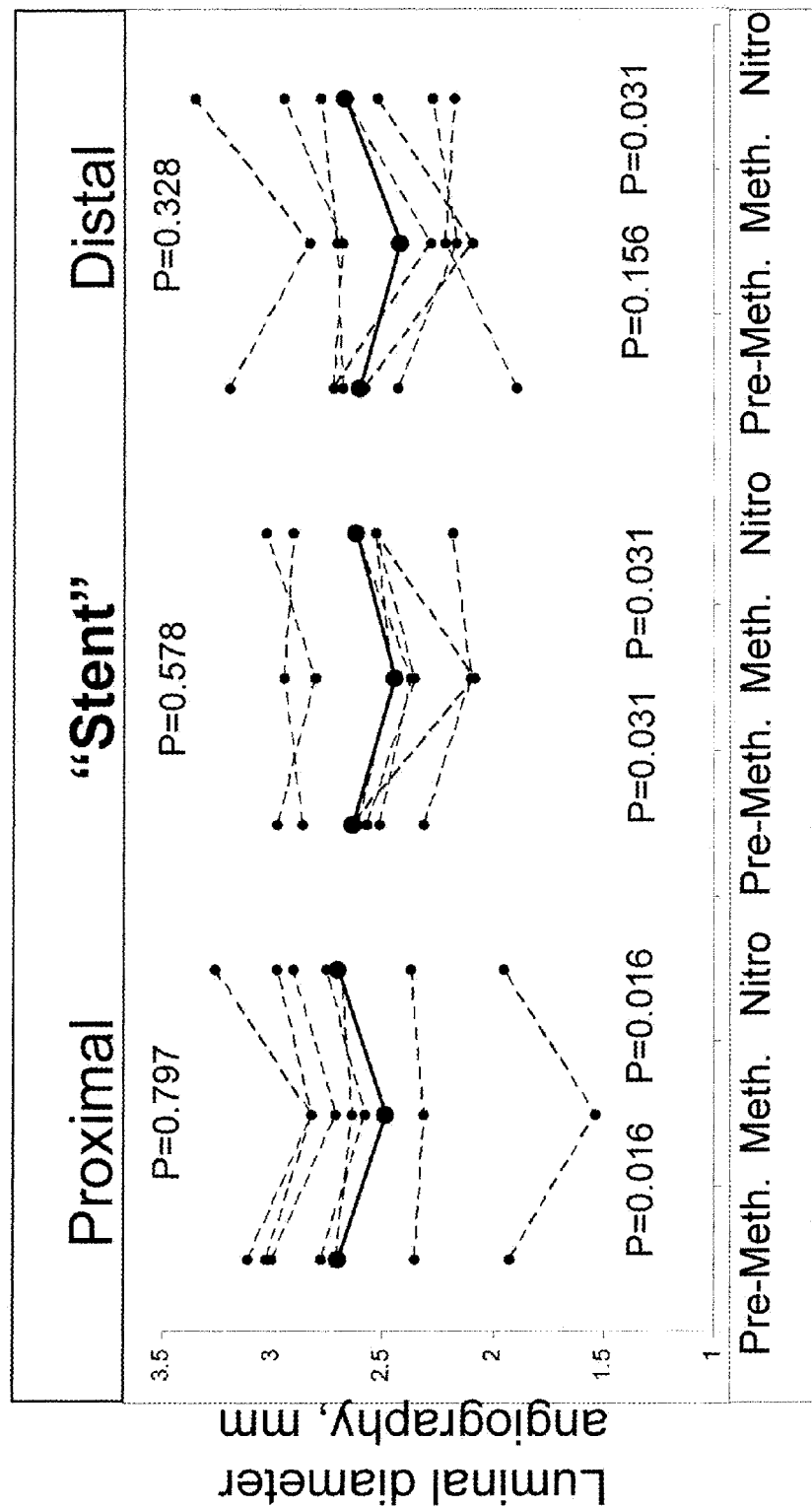
FIG. 20A shows angiography measurements for patients treated with methergine and nitroglycerine at 2 year follow-up.

FIG. 20A shows angiography measurements for patients treated with methergine and nitroglycerine. For each patient, the luminal diameter was measured pre-methergine treatment, with methergine treatment, and with nitroglycerine treatment. There was significant vasoconstriction in proximal and stented segments. After nitroglycerin, the three segments (proximal, stented, and distal) dilated significantly with their diameters returning to their baseline values.

Figure 20B:
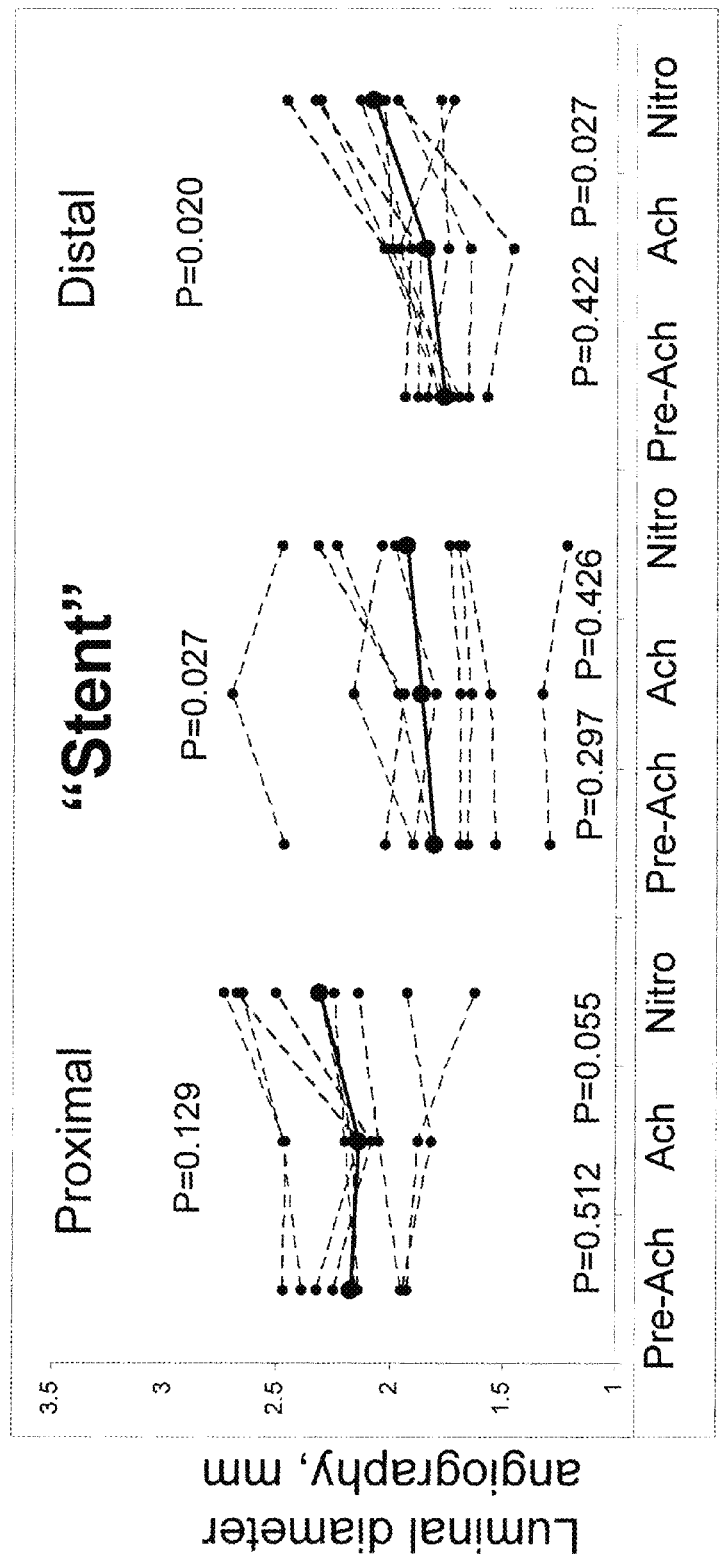
FIG. 20B shows angiography measurements for patients treated with acetylcholine and nitroglycerin at 2 year follow-up.
Figure 21:
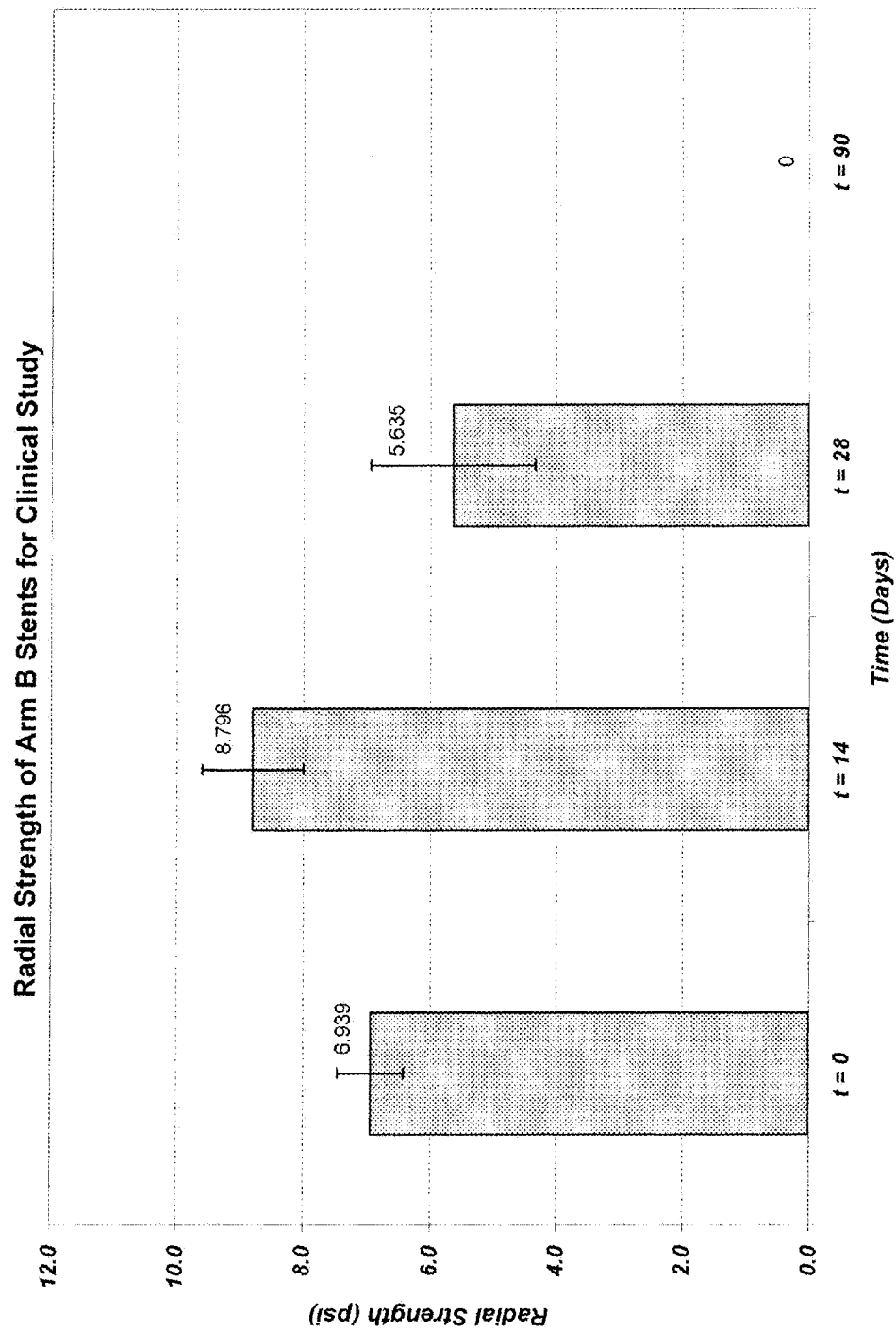
FIG. 21 depicts the results of in vitro radial strength testing of one arm of bioabsorbable stents manufactured for clinical trial.

FIG. 20B shows angiography measurements for patients treated with acetylcholine and nitroglycerin. Five patients had vasodilation of at least 3% in mean luminal diameter. Nitrates induced a significant vasodilatation in the stented and distal segments. These results show the restoration of vasomotor function in the stented segment.

Table 12 provides vessel measurements for one patient at 2 years that demonstrate vasoconstriction and vasocompression. The reappearance of vasomotion of the stented and persistent segments in response to methergine or acetylcholine suggests that vessel vasoreactivity has been restored and that a physiological response to vasoactive stimulus might occur anew. Unlike previous studies reporting endothelial dysfunction in the distal segment, this study shows vasomotor tone in the stented segment, once the scaffolding properties of the stent had disappeared as a result of its bioabsorption. Five of the nine patients tested with acetylcholine showed vasodilatation (at least 3% of the mean diameter) during the highest dose infused. This suggests direct vasodilator or flow-mediated response to acetylcholine and thus the presence of functionally active endothelium at the site of the stent implantation.

TABLE 12

Vessel diameters pre- and post-methergine and post nitroglycerine treatment at 2 years follow-up for one patient.

|  | Pre-Methergine | Post Methergine (5 min) | Change N (%) | Post Nitroglycerine | Change N (%) |
|---|---|---|---|---|---|
| In-Stent Mean Diameter | 2.62 mm | 1.98 mm | −0.64 mm (−24.4%) | 2.58 mm | +0.60 mm (+30.3%) |
| Mean Diameter 2-17 mm Distal to Stent | 2.70 mm | 2.08 mm | −0.62 mm (−23.0%) | 2.62 mm | +0.54 mm (+26.0%) |

Multi-Slice CT Results

Multi-slice CT imaging was done 18 months after the index procedure. Single or dual-source, 64-slice spiral CT with intravenous contrast enhancement and electrocardiograph-gated image reconstruction was done (Siemens Definition, Forchheim, Germany [n=18]; GE Lightspeed, Milwaukee, USA [n=5]; Philips Brilliance, Best, Netherlands [n=2]). The amount of in-stent stenosis was measured using a semi-automated software program for vessel segmentation and lumen area quantification (Circulation, Siemens, Forchheim, Germany).

The BVS stent is undetected by multi-slice CT, apart from the platinum markers at each end of the stent. Along the automatically constructed center-lumen line, the cross-sectional lumen area was measured at 0.3 mm longitudinal intervals within the stented segment. The lumen diameter was calculated from the measured area, assuming a circular shape of the lumen area. Severity of in-stent diameter stenosis or area stenosis was calculated as a ratio of the smallest in-stent lumen diameter or area and the reference vessel diameter or area, which was calculated by interpolation of the proximal and distal lumen reference. Additionally, the length of vessel was measured between the platinum stent markers. The quantitative results in Table 13 show that all stents were qualitatively patent.

TABLE 13

Quantitative multi-slice CT results.

|  | 2 years |
|---|---|
| N | 24 |
| Mean luminal area (mm$^2$) | 5 · 2 (1.3) |
| Minimal luminal area (mm$^2$) | 3 · 6 (0.9) |
| Reference area (mm$^2$) | 5 · 5 (1.0) |
| Mean area stenosis (%) | 34% (15) |
| Minimal diameter (mm) | 2 · 12 (0.26) |
| Mean diameter stenosis (%) | 19% (9) |

Summary of Cardiac Events for Intent to Treat Population

Table 14 summarizes the cardiac events of the intent to treat clinical population. Patients were followed out to two years. No stent thrombosis and no major adverse cardiac events were observed. No new MACE events between 6 months and 2 years. No stent thrombosis was observed up to 2 years.

TABLE 14

Cardiac events of intent to treat population.

|  | Hierarchical | | | |
|---|---|---|---|---|
|  | 6 Months 30 Patients | 12 Months 29 Patients** | 18 Months 29 Patients** | 2 Years 28 Patients** |
| Ischemia Driven MACE (%) | 3.3% (1)* | 3.4% (1)* | 3.4% (1)* | 3.6% (1)* |
| Cardiac Death (%) | 0.0% (0) | 0.0% (0) | 0.0% (0) | 0.0% (0) |
| MI (%) | 3.3% (1)* | 3.4% (1)* | 3.4% (1)* | 3.6% (1)* |
| Q-Wave MI | 0.0% (0) | 0.0% (0) | 0.0% (0) | 0.0% (0) |
| Non Q-Wave MI | 3.3% (1)* | 3.4% (1)* | 3.4% (1)* | 3.6% (1)* |
| Ischemia Driven TLR (%) | 0.0% (0) | 0.0% (0) | 0.0% (0) | 0.0% (0) |
| by PCI | 0.0% (0) | 0.0% (0) | 0.0% (0) | 0.0% (0) |
| by CABG | 0.0% (0) | 0.0% (0) | 0.0% (0) | 0.0% (0) |

*Same patient - this patient also underwent a TLR, not qualified as ID-TLR (DS = 42%)

**One patient missed the 9, 12, 18 month and 2 year visits. One patient died from a non-cardiac cause 706 days post-procedure MACE = major adverse cardiac events MI = post-myocardial infarction (MI)

TLR = target lesion revascularization

ID-TLR = ischemia driven target lesion revascularization

PCI = post-percutaneous coronary intervention

CABG = Coronary Artery Bypass Graft

In Vitro Testing of Radial Strength

The radial strength of BVS stent was tested in vitro at four time points. The tests show the effect of degradation on radial strength. The types of stents used in the in vitro tests are the same as those used in human clinical trials. The results of these trials are discussed below. The in vitro tests were performed by immersing stents in a phosphate buffered saline solution simulating a vascular environment.

The radial strength of stents in the four arms was tested. Each arm initially contained 3 stents. The radial strength of the 3 stents was tested at time zero or no exposure to the solution, two weeks, 28 days, and three months. The radial strength was measured by a flat plate compression test using a machine obtained from Instron in Canton, Mass.

The representative results of the in vitro tests from arm B stents are shown in FIG. 20. The results indicate a small change in radial strength between time zero and 28 days. The radial strength decreased at 28 days and was undetectable at three months. Therefore, the stent lost radial strength between 28 days and three months.

"Radial strength" of a stent is defined as the pressure at which a stent experiences irrecoverable deformation.

"Stress" refers to force per unit area, as in the force acting through a small area within a plane. Stress can be divided into components, normal and parallel to the plane, called normal stress and shear stress, respectively. Tensile stress, for example, is a normal component of stress applied that leads to expansion (increase in length). In addition, compressive stress is a normal component of stress applied to materials resulting in their compaction (decrease in length). Stress may result in deformation of a material, which refers to a change in length. "Expansion" or "compression" may be defined as the increase or decrease in length of a sample of material when the sample is subjected to stress.

"Strain" refers to the amount of expansion or compression that occurs in a material at a given stress or load. Strain may be expressed as a fraction or percentage of the original length, i.e., the change in length divided by the original length. Strain, therefore, is positive for expansion and negative for compression.

"Strength" refers to the maximum stress along an axis which a material will withstand prior to fracture. The ultimate strength is calculated from the maximum load applied during the test divided by the original cross-sectional area.

"Modulus" may be defined as the ratio of a component of stress or force per unit area applied to a material divided by the strain along an axis of applied force that result from the applied force. For example, a material has both a tensile and a compressive modulus.

The tensile stress on a material may be increased until it reaches a "tensile strength" which refers to the maximum tensile stress which a material will withstand prior to fracture. The ultimate tensile strength is calculated from the maximum load applied during a test divided by the original cross-sectional area. Similarly, "compressive strength" is the capacity of a material to withstand axially directed pushing forces. When the limit of compressive strength is reached, a material is crushed.

The underlying structure or substrate of an implantable medical device, such as a stent can be completely or at least in part made from a biodegradable polymer or combination of biodegradable polymers, a biostable polymer or combination of biostable polymers, or a combination of biodegradable and biostable polymers. Additionally, a polymer-based coating for a surface of a device can be a biodegradable polymer or combination of biodegradable polymers, a biostable polymer or combination of biostable polymers, or a combination of biodegradable and biostable polymers.

It is understood that after the process of degradation, erosion, absorption, and/or resorption has been completed, no part of the stent will remain or in the case of coating applications on a biostable scaffolding, no polymer will remain on the device. In some embodiments, very negligible traces or residue may be left behind. For stents made from a biodegradable polymer, the stent is intended to remain in the body for a duration of time until its intended function of, for example, maintaining vascular patency and/or drug delivery is accomplished.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method of treating a diseased section of a blood vessel, comprising:
   implanting a bioabsorbable polymeric stent comprising a scaffolding composed of a pattern of struts at a diseased section of a blood vessel to form a stented segment comprising the stent and a vessel wall surrounding a lumen at the diseased section,
   wherein implanting comprises deploying the stent from a crimped diameter to a diameter of 3 mm,
   wherein a reference vessel diameter is 3 mm and a diameter stenosis of the diseased section of the blood vessel pre-implantation is greater than 50%,
   wherein the vessel wall comprises a plaque region including a necrotic core component and a fibrous component, wherein at pre-implantation and immediately following implantation of the stent the necrotic core component is in contact with the lumen, and
   wherein as the stent degrades the fibrous component covers the necrotic core component so that the necrotic core component is no longer in contact with the lumen.

2. The method of claim 1, wherein the crimped diameter is 1.346 mm.

3. The method of claim 1, wherein the scaffolding is made from poly(L-lactide).

4. A method of treating a diseased section of a blood vessel, comprising:
   implanting a bioabsorbable polymeric stent comprising a scaffolding composed of a pattern of struts at a diseased section of a blood vessel to form a stented segment comprising the stent and a vessel wall surrounding a lumen at the diseased section,
   wherein implanting comprises deploying the stent from a crimped diameter to a diameter of 3.5 mm,
   wherein a reference vessel diameter is 3 mm and a diameter stenosis of the diseased section of the blood vessel pre-implantation is greater than 50%,
   wherein the vessel wall comprises a plaque region including a necrotic core component and a fibrous component, wherein at pre-implantation and immediately following implantation of the stent the necrotic core component is in contact with the lumen, and
   wherein as the stent degrades the fibrous component covers the necrotic core component so that the necrotic core component is no longer in contact with the lumen.

5. The method of claim 4, wherein the crimped diameter is 1.346 mm.

6. The method of claim 4, wherein the scaffolding is made from poly(L-lactide).

\* \* \* \* \*